(12) United States Patent
Foley et al.

(10) Patent No.: US 8,308,803 B2
(45) Date of Patent: Nov. 13, 2012

(54) METHODS AND INSTRUMENTS FOR ENDOSCOPIC INTERBODY SURGICAL TECHNIQUES

(75) Inventors: Kevin T. Foley, Germantown, TN (US); John L. White, Bartlett, TN (US); Bradley T. Estes, Memphis, TN (US); Mingyan Liu, Bourg-la-Reine (FR); Loic Josse, Palaja (FR); Jeffrey D. Moore, Horn Lake, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1332 days.

(21) Appl. No.: 12/009,823

(22) Filed: Jan. 22, 2008

(65) Prior Publication Data

US 2008/0208258 A1   Aug. 28, 2008

Related U.S. Application Data

(63) Continuation of application No. 10/455,678, filed on Jun. 5, 2003, now Pat. No. 7,320,688, which is a continuation of application No. 09/692,932, filed on Oct. 20, 2000, now Pat. No. 6,575,899.

(60) Provisional application No. 60/160,550, filed on Oct. 20, 1999.

(51) Int. Cl.
*A61F 2/44*   (2006.01)
(52) U.S. Cl. .................................................. 623/17.16
(58) Field of Classification Search ..... 623/17.11–17.16
See application file for complete search history.

(56) References Cited

U.S. PATENT DOCUMENTS

| | | |
|---|---|---|
| 3,486,505 A | 12/1969 | Morrison |
| 3,848,601 A | 11/1974 | Ma et al. |
| 3,964,480 A | 6/1976 | Froning |
| 4,059,115 A | 11/1977 | Jumashev et al. |
| 4,538,594 A | 9/1985 | Boebel et al. |
| 4,545,374 A | 10/1985 | Jacobson |
| 4,573,448 A | 3/1986 | Kambin |
| 4,610,243 A | 9/1986 | Ray |
| 4,743,256 A | 5/1988 | Brantigan |
| 4,899,729 A | 2/1990 | Gill et al. |

(Continued)

FOREIGN PATENT DOCUMENTS

EP    0 077 159 A1    4/1983

(Continued)

OTHER PUBLICATIONS

Sofamor Danek, The Spine Specialist (1994); Micro-endo Systems . . . Creating the Future of Spinal Endoscopy.

(Continued)

*Primary Examiner* — Alvin Stewart
*Assistant Examiner* — Summer Kostelnik

(57) ABSTRACT

This invention relates to methods and instruments for performing a surgical procedure in a disc space between adjacent vertebrae. A cannula is inserted to create a working channel through the skin and tissue of a patient using a transformational approach to the disc space. A viewing element is used to visualize working end of the cannula and the disc space. A facetectomy is performed through the working channel to access the disc space. The disc space is prepared with various instruments, such as distractors, shims, chisels and distractor-cutters that extend through the working channel. At least implant is inserted into the disc space. The procedure allows bi-lateral support of the adjacent vertebrae with the at least one implant inserted via a unitary, minimally invasive approach to disc space.

18 Claims, 17 Drawing Sheets

U.S. PATENT DOCUMENTS

| | | | |
|---|---|---|---|
| 5,195,541 A | 3/1993 | Obenchain | |
| 5,241,972 A | 9/1993 | Bonati | |
| 5,313,962 A | 5/1994 | Obenchain | |
| 5,334,194 A | 8/1994 | Mikhail | |
| 5,354,302 A | 10/1994 | Ko | |
| 5,395,317 A | 3/1995 | Kambin | |
| 5,423,825 A | 6/1995 | Levine | |
| 5,431,658 A | 7/1995 | Moskovich | |
| 5,439,464 A | 8/1995 | Shapiro | |
| 5,472,426 A | 12/1995 | Bonati et al. | |
| 5,484,437 A | 1/1996 | Michelson | |
| 5,489,307 A | 2/1996 | Kuslich et al. | |
| 5,551,947 A | 9/1996 | Kaali | |
| 5,571,109 A | 11/1996 | Bertagnoli | |
| 5,720,748 A | 2/1998 | Kuslich et al. | |
| 5,722,977 A | 3/1998 | Wilhelmy | |
| 5,772,661 A | 6/1998 | Michelson | |
| 5,785,710 A | 7/1998 | Michelson | |
| 5,792,044 A * | 8/1998 | Foley et al. | 600/114 |
| 5,797,909 A | 8/1998 | Michelson | |
| 5,803,904 A | 9/1998 | Mehdizadeh | |
| 5,899,908 A | 5/1999 | Kuslich et al. | |
| 5,902,231 A | 5/1999 | Foley et al. | |
| 5,904,686 A | 5/1999 | Zucherman et al. | |
| 5,954,635 A | 9/1999 | Foley et al. | |
| 5,968,098 A | 10/1999 | Winslow | |
| 5,984,967 A | 11/1999 | Zdeblick et al. | |
| 6,004,326 A | 12/1999 | Castro et al. | |
| 6,042,582 A | 3/2000 | Ray | |
| 6,059,790 A | 5/2000 | Sand et al. | |
| 6,063,088 A | 5/2000 | Winslow | |
| 6,080,155 A | 6/2000 | Michelson | |
| 6,083,225 A | 7/2000 | Winslow et al. | |
| 6,086,595 A | 7/2000 | Yonemura et al. | |
| 6,096,038 A | 8/2000 | Michelson | |
| 6,113,602 A | 9/2000 | Sand | |
| 6,120,506 A | 9/2000 | Kohrs et al. | |
| 6,126,664 A | 10/2000 | Troxell et al. | |
| 6,146,420 A * | 11/2000 | McKay | 623/17.16 |
| 6,152,871 A | 11/2000 | Foley et al. | |
| 6,156,040 A | 12/2000 | Yonemura et al. | |
| 6,174,311 B1 | 1/2001 | Branch et al. | |
| 6,210,412 B1 | 4/2001 | Michelson | |
| 6,224,607 B1 | 5/2001 | Michelson | |
| 6,241,770 B1 * | 6/2001 | Michelson | 623/17.11 |
| 6,500,180 B1 | 12/2002 | Foley et al. | |
| 6,575,899 B1 | 6/2003 | Foley et al. | |
| 7,320,688 B2 | 1/2008 | Foley et al. | |
| 2001/0016776 A1 | 8/2001 | Zucherman et al. | |
| 2005/0154396 A1 | 7/2005 | Foley et al. | |

FOREIGN PATENT DOCUMENTS

| | | |
|---|---|---|
| FR | 2 714 285 A1 | 6/1995 |
| WO | WO 98/04202 | 2/1998 |
| WO | WO 99/09896 | 3/1999 |
| WO | WO 99/52453 | 10/1999 |
| WO | WO 99/63891 | 12/1999 |
| WO | WO 00/44320 | 8/2000 |
| WO | WO 00/45709 | 8/2000 |

OTHER PUBLICATIONS

Sofamor Danek; Scott H. Kitchel, M.D., Oregon Health Sciences Univerisity, Eugene, Oregon; Anterior Instrumentation, pp. 1-20.

Hallett H. Mathews, M.D., Associate Professor Department of Orthopaedic Surgery, Medical College of Virginia; Spinal Endoscopy Evolution, Applications & Foundations, pp. 1-44.

David A. Ditsworth, M.D., Endoscopic Transforaminal Lumbar Discectomy and Reconfiguration: A Postero-lateral Approach into the Spinal Canal, Surg Neural 1998; 49:588-98; 1998 by Elsevier Science Inc.

* cited by examiner

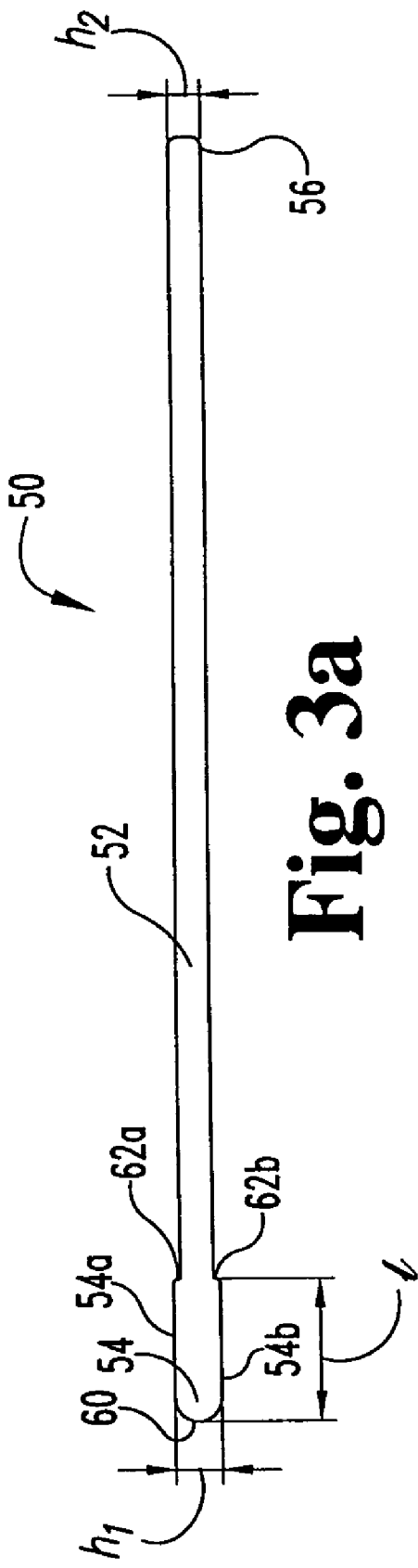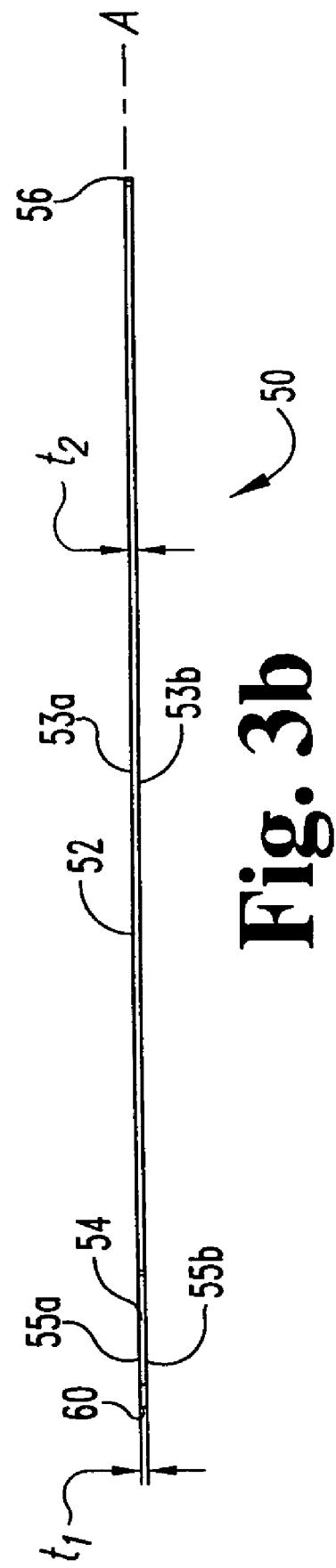
Fig. 3a
Fig. 3b

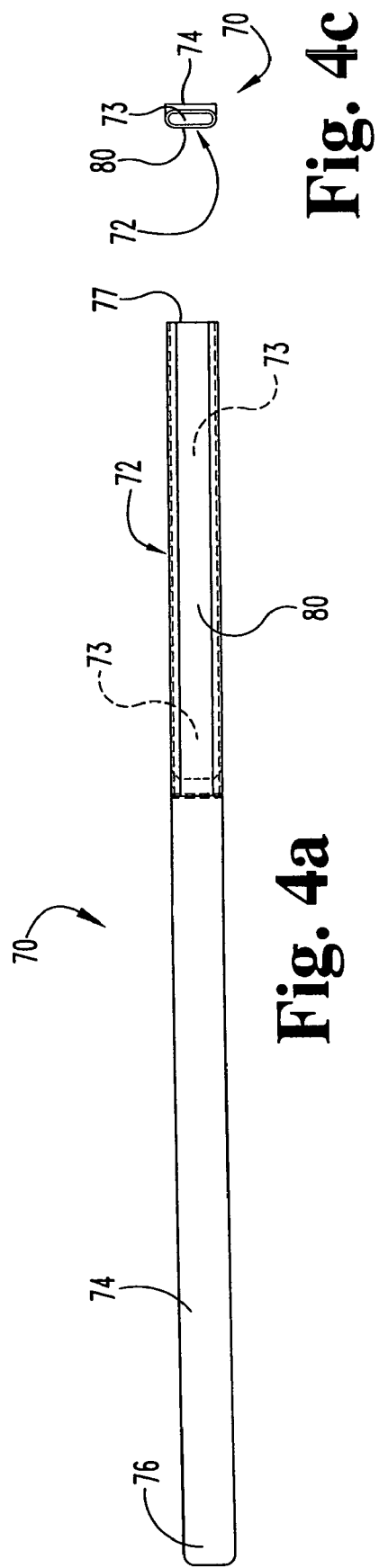
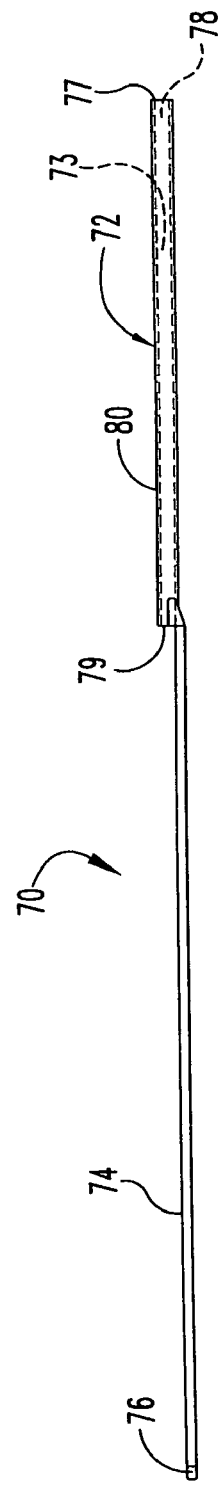
Fig. 4a
Fig. 4b
Fig. 4c

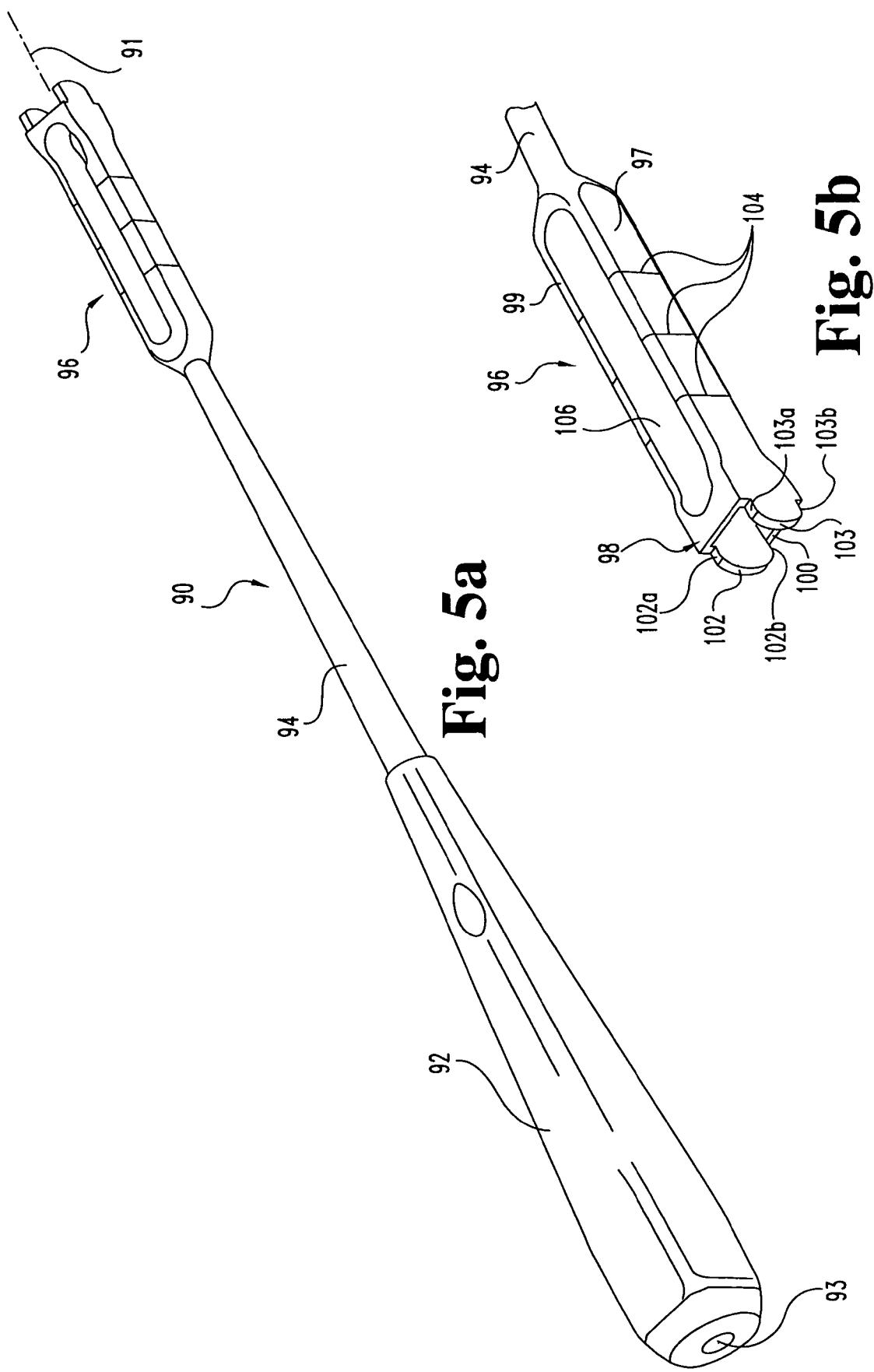

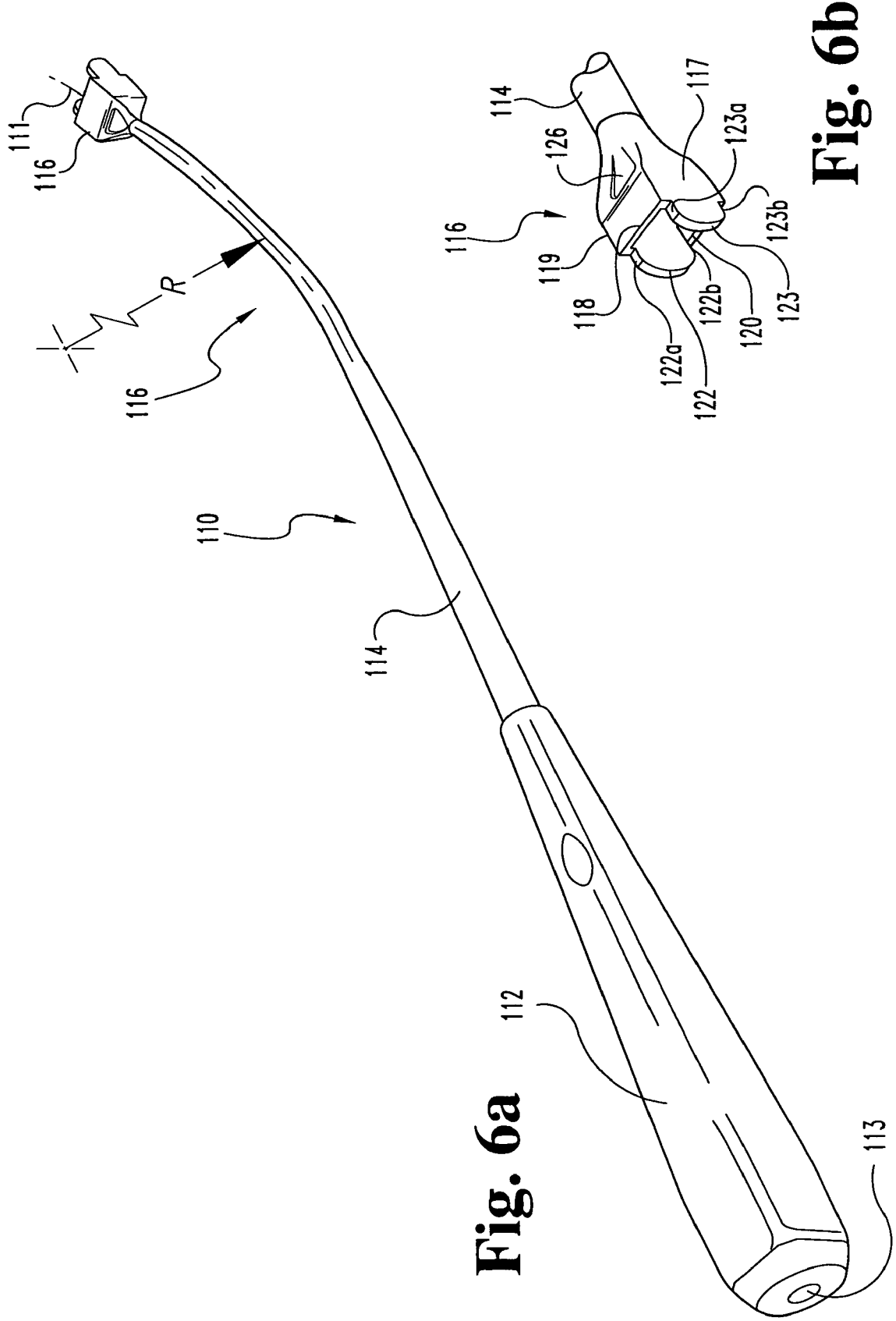

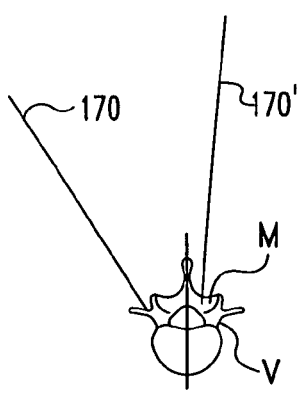
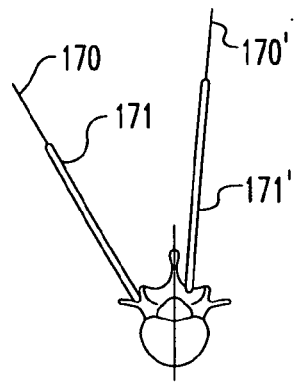
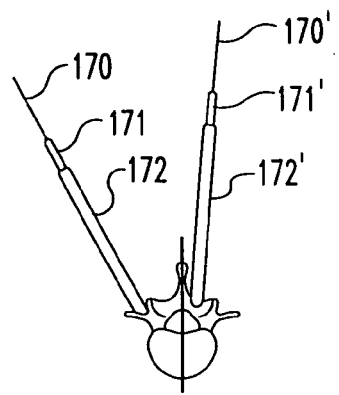
Fig. 10a  Fig. 10b  Fig. 10c
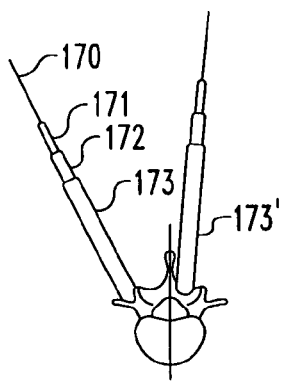
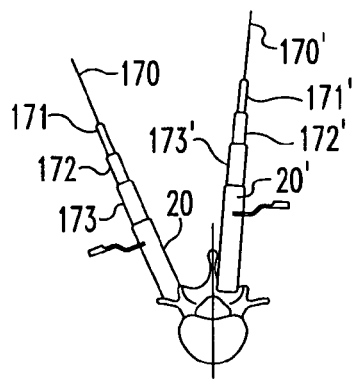
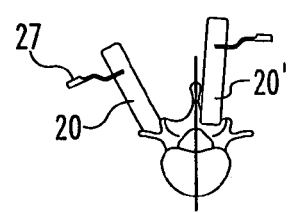
Fig. 10d  Fig. 10e  Fig. 10f
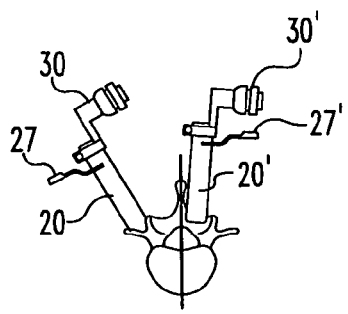
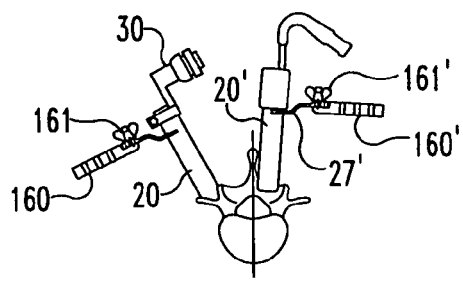
Fig. 10g  Fig. 10h

METHODS AND INSTRUMENTS FOR ENDOSCOPIC INTERBODY SURGICAL TECHNIQUES

CROSS-REFERENCE TO RELATED APPLICATIONS

This application is a continuation of U.S. patent application Ser. No. 10/455,678, filed on Jun. 5, 2003, issuing as U.S. Pat. No. 7,320,688; which is a continuation of U.S. patent application Ser. No. 09/692,932 filed on Oct. 20, 2000, and now issued as U.S. Pat. No. 6,575,899; which claims the benefit of the filing date of Provisional Application Ser. No. 60/160,550, filed Oct. 20, 1999. The referenced applications are incorporated herein by reference in their entirety.

FIELD OF THE INVENTION

The present invention relates to techniques for use in interbody spinal procedures and instruments for performing such procedures. More specifically, but not exclusively, the present invention relates to methods and instruments for endoscopic interbody surgical techniques.

BACKGROUND

Normally intervertebral discs, which are located between endplates of adjacent vertebrae, stabilize the spine and distribute forces between the vertebrae and cushion vertebral bodies. The spinal discs may be displaced or damaged due to trauma, disease or aging. A herniated or ruptured annulus fibrosis may result in nerve damage, pain, numbness, muscle weakness, and even paralysis. Furthermore, as a result of the normal aging processes, discs dehydrate and harden, thereby reducing the disc space height and producing instability of the spine and decreased mobility. Most typically surgical correction of a disc space includes a discectomy (surgical removal of a portion or all of the intervertebral disc material.) The discectomy is often followed by fusion of the adjacent vertebrae to alleviate the pain, abnormal joint mechanics, premature development of arthritis, and nerve damage.

Traditional surgical procedures for correction of disc space pathologies can cause significant trauma to the intervening tissues. These open procedures often require a long incision, extensive muscle stripping, prolonged retraction of tissues, denervation and devascularization of tissue. Most of these surgeries require room time of several hours and several weeks of post-operative recovery time due to the use of general anesthesia and the destruction of tissue during the surgical procedure. In some cases, these invasive procedures lead to permanent scarring and pain that can be more severe than the pain leading to the surgical intervention.

One type of open procedure that attempts to minimize trauma to tissue that occurs with an open procedure uses a transformational approach to the disc space. This approach is advantageous in that it allows placement of one or more implants into the disc space with a single incision. However, this approach still suffers from the drawback that the posterior musculature and tissue at the surgical site suffer trauma and damage due to the incision and retraction of tissue at the surgical site.

Minimally invasive surgical techniques are particularly desirable for spinal and neurosurgical applications because of the need for access to locations deep within the body and the danger of damage to vital intervening tissues. The development of percutaneous spinal procedures has yielded a major improvement in reducing recovery time and post-operative pain because they require minimal, if any, muscle dissection and they can be performed under local anesthesia. For example, U.S. Pat. No. 4,545,374 to Jacobson discloses a percutaneous lumbar discectomy using a lateral approach, preferably under fluoroscopic X-ray. This procedure is limited because, among other limitations, it does not provide direct visualization of the discectomy site.

Other procedures have been developed which include arthroscopic visualization of the spine and intervening structure. U.S. Pat. Nos. 4,573,448 and 5,395,317 to Kambin disclose percutaneous decompression of herniated discs with a posterolateral approach. Fragments of the herniated disc are evacuated through a cannula positioning against the annulus. The '317 Kambin patent discloses a biportal procedure which involves percutaneously placing both a working cannula and a visualization cannula for an endoscope. This procedure allows simultaneous visualization and suction, irrigation and resection in disc procedures. These approaches seek to avoid damage to soft tissue structures and the need for bone removal through a channel. However, these approaches are limited because they do not address, for example, disc space distraction, disc space preparation and implant insertion into the disc space. The approach of the '317 patent also requires multiple entries into the patient, and the approach of the '448 patent does not provide for direct visualization of the working space.

Further examples of instruments and methods for performing spinal surgeries using minimally invasive approaches are found in U.S. Pat. Nos. 5,792,044 and 5,902,231 to Foley et al. The present invention is also directed to further improvements and techniques using a minimally invasive approach for performing spinal surgery.

SUMMARY

One aspect of the present invention includes inserting one or more interbody fusion devices in a spinal disc space using a minimally invasive, transformational approach. Another aspect of the present invention includes inserting performing surgical procedures in a spinal disc space using a minimally invasive, transformational approach.

In accordance with another aspect of the invention, a method for performing a surgical procedure in a disc space between adjacent vertebrae is provided. The method includes inserting a cannula to create a working channel through the skin and tissue of a patient using a transformational approach to the disc space; inserting a viewing element through the working channel; and preparing the disc space through the working channel for insertion of at least one interbody fusion device. In one form, a facetectomy is performed through the working channel to access the disc space;

In accordance with a further aspect of the invention, a method for inserting at least one interbody fusion device in a disc space between adjacent vertebrae is provided. The method includes creating a working channel to the disc space through the skin and tissue of a patient using a transformational approach to the disc space; preparing the disc space through the working channel for bi-lateral placement of the at least one fusion device; and inserting the at least one fusion device into the disc space through the working channel so that the adjacent vertebrae are bi-laterally supported by the at least one interbody fusion device.

In accordance with yet another aspect of the invention, a method of restoring disc height between adjacent vertebrae of a patient is provided. The method includes inserting a cannula through the skin and tissue of the patient to create a working channel to the disc space; distracting the adjacent vertebrae to a disc space height with a distractor extending through the cannula into the disc space; and inserting a shim through the cannula into the disc space adjacent the distractor. The shim has a blade with a height corresponding to the distracted disc space height so that the blade contacts the endplates of the adjacent vertebrae.

In accordance with a further aspect of the invention, a method of preparing a disc space for insertion of an implant between adjacent vertebrae of a patient is provided. The method includes inserting a cannula through the skin and tissue of the patient to create a working channel to the disc space; distracting the disc space to a disc space height by positioning a distractor in the disc space, the distractor being attached to a stem that extends through the working channel, the distractor including a body portion extending between a leading end and a trailing end, the body portion including an upper surface and an opposite lower surface and opposite first and second sidewalls extending between the upper and lower surfaces, the distractor further including a first flange and a second flange each extending proximally from the leading end of the body portion towards the trailing end, the first flange forming a slot with the first sidewall and the second flange forming a slot with the second sidewall; inserting a cutter through the working channel, the cutter having an upper member with an upper cutting edge and a lower member with a lower cutting edge and a pair of opposite sidewalls extending between the upper and lower members; and cutting the adjacent vertebrae by advancing the cutter over the body portion of the distractor such that each sidewall of the cutter is received in a respective one of the slots.

Further objects, features, benefits, aspects and advantages of the present invention shall become apparent from the detailed drawings and descriptions provided herein.

BRIEF DESCRIPTION OF THE DRAWINGS

FIG. 3(a) is a top plan view of a shim having application in the present invention.

FIG. 3(b) is a side elevational view of the shim of FIG. 3(a).

FIG. 4(a) is a top plan view a driver for the shim of FIG. 3(a).

FIG. 4(b) is a side elevational view of the driver of FIG. 4(a).

FIG. 4(c) is an end view of the driver of FIG. 4(a).

FIG. 5(a) is a perspective view of one embodiment of a chisel having application in the present invention.

FIG. 5(b) is an enlarged perspective view of the cutting head of the chisel of FIG. 5(a).

FIG. 6(a) is a perspective view of one embodiment of another chisel having application in the present invention.

FIG. 6(b) is an enlarged perspective view of the cutting head of the chisel of FIG. 6(a).

FIGS. 10(a)-(h) depict the steps of various methods of accessing the disc space according to the present invention.

DETAILED DESCRIPTION OF THE ILLUSTRATED EMBODIMENTS

Figure 1:
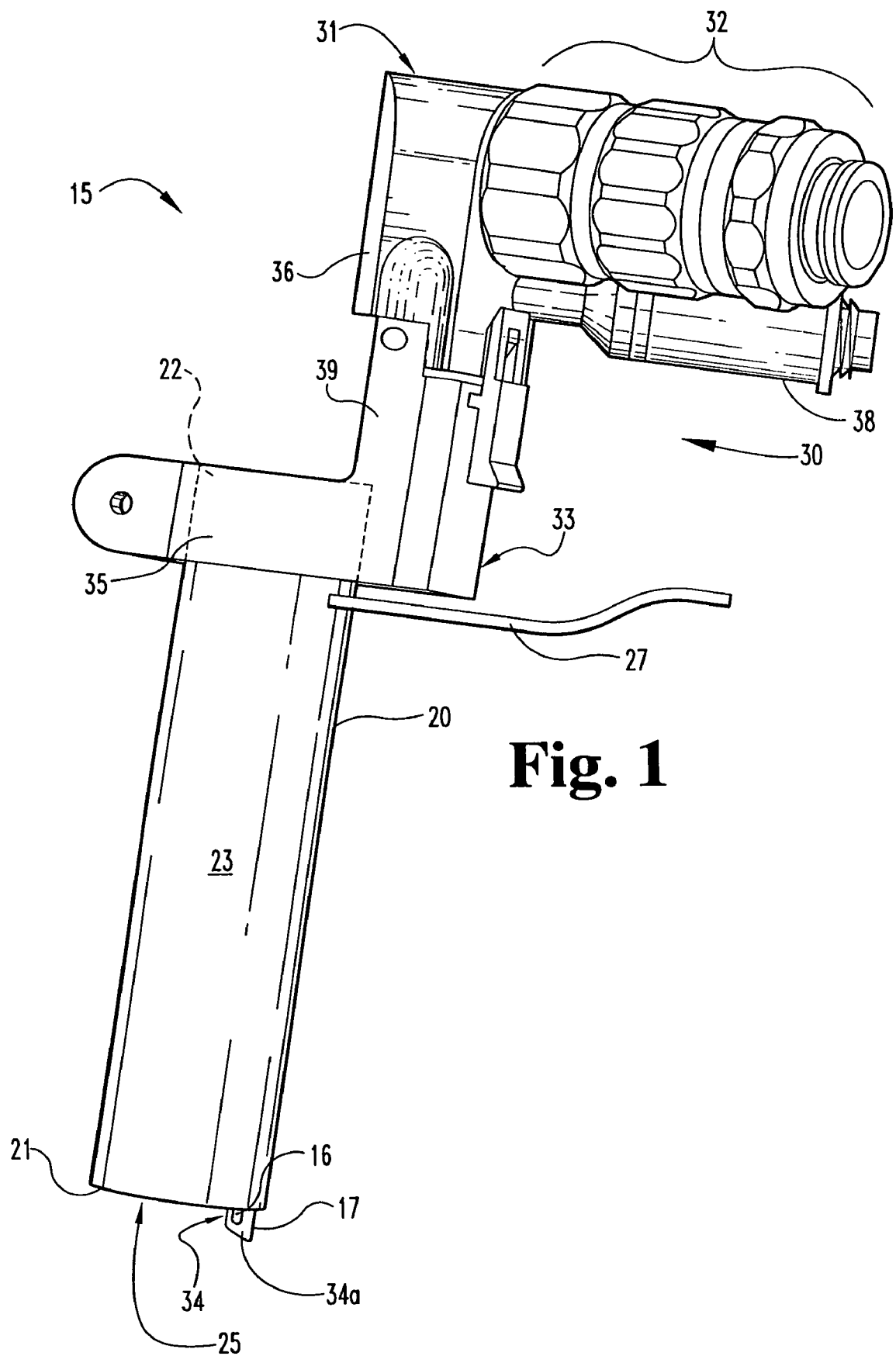
FIG. 1 is a side perspective view of a cannula and viewing element having application in the present invention.

For the purposes of promoting an understanding of the principles of the present invention, reference will now be made to the embodiments illustrated in the drawings, and specific language will be used to describe the same. It will nevertheless be understood that no limitation of the scope of the invention is intended thereby. Any alterations and further modification in the described processes, systems, or devices, and any further applications of the principles of the invention as described herein are contemplated as would normally occur to one skilled in the art to which the invention relates.

Aspects of the present invention have application to a wide range of surgical procedures, and particularly spinal procedures such as laminotomy, laminectomy, foramenotomy, facetectomy and discectomy, using a posterior, postero-lateral, or a lateral approach to the disc space. The devices and instruments of present invention have application to inventive surgical techniques that permit each of these several types of surgical procedures to be performed via a single working channel. The present invention also has application to surgical techniques for preparing a disc space for insertion of an implant into the disc space. The present invention further has application in a transformational, minimally invasive surgical procedure in which the disc space is prepared for insertion of one or more implants into the disc space with a unilateral approach.

Referring now to FIG. 1, one example of a cannula assembly 15 for providing an endoscopic, minimally invasive approach to disc space is provided. It should be understood that other shapes for cannula assembly 15 are also contemplated herein, so long as the cannula assembly includes a protective sleeve for providing a minimally invasive approach to the disc space and visualization of the surgical site. Cannula assembly 15 includes a cannula 20 defining a working channel 25 between a working end 21 and a proximal second end 22. The length of cannula 20 is sized so that second end 22 is positioned above the skin of the patient when cannula 20 is positioned at the surgical site.

Cannula assembly 15 also includes an endoscope assembly 30 mountable on cannula 20. Endoscope assembly 30 includes an upper end 31 having a viewing apparatus 32, such as an eyepiece, an illumination element 38, and an elongated viewing element 34 disposed within the working channel 25. Viewing element 34 has a distal end 34a positionable adjacent the distal working end 21 of cannula 20. The particular viewing element used is not critical to the invention. Any suitable viewing element is contemplated that allows visualization of the surgical site is contemplated. In the illustrated embodiment, distal end 34a of viewing element 34 is extendable from and retractable into cannula 20. Viewing element 34 is further rotatable about and positionable at various locations around the working channel 25. In one embodiment, the elongated viewing element 30 includes a fiber optic scope and a lens at the distal end 34a. The fiber optic scope includes illumination fibers and image transmission fibers (not shown). Alternatively, the viewing element may be a rigid endoscope, or an endoscope having a steerable or bendable tip.

Cannula assembly 15 contemplates any configuration or apparatus allowing the optics to be supported adjacent the working channel 25. In the embodiment shown in FIG. 1, a fixture 33 is provided for mounting endoscope assembly 30 on cannula 20 with elongated viewing element 34 disposed in working channel 25 of cannula 20. Fixture 33 includes a clamp 35 attachable to the second end 22 of cannula 20. Clamp 35 is clamped on outer surface 23 of cannula and maintains the opening for working channel 25 at proximal end 22. The working channel 25 is sized to receive one or more surgical tools therethrough for performing surgical procedures through cannula 20.

Cannula assembly 15 may also include irrigation and aspiration components 16 and 17 extending along viewing element 34 in cannula 20. Endoscope assembly 30 includes a detachable endoscope 36 that is removable from clamp 35. One type of modular endoscope assembly contemplated by the present invention is described in U.S. patent application Ser. No. 09/160,882, filed Sep. 25, 1998, which application is incorporated herein by reference in its entirety. Cannulas and endoscope assemblies are also described in U.S. Pat. Nos. 5,792,044 and 5,902,231 to Foley et al., which patents are also incorporated herein by reference in their entirety.

The present invention also contemplates instruments for use with the cannula assembly 15 to prepare a disc space for insertion of one or more implants and inserting the implants in the disc space. Specific instruments include distractors, shims, chisels, distractor-cutters, implant holders, reamers, and drills. Other instruments for performing surgical procedures on the vertebral bodies or in the disc space are also contemplated herein as would occur to those skilled in the art so long as the instruments are capable of being used in a minimally invasive procedure through working channel 25 of cannula 20.

Figure 2:
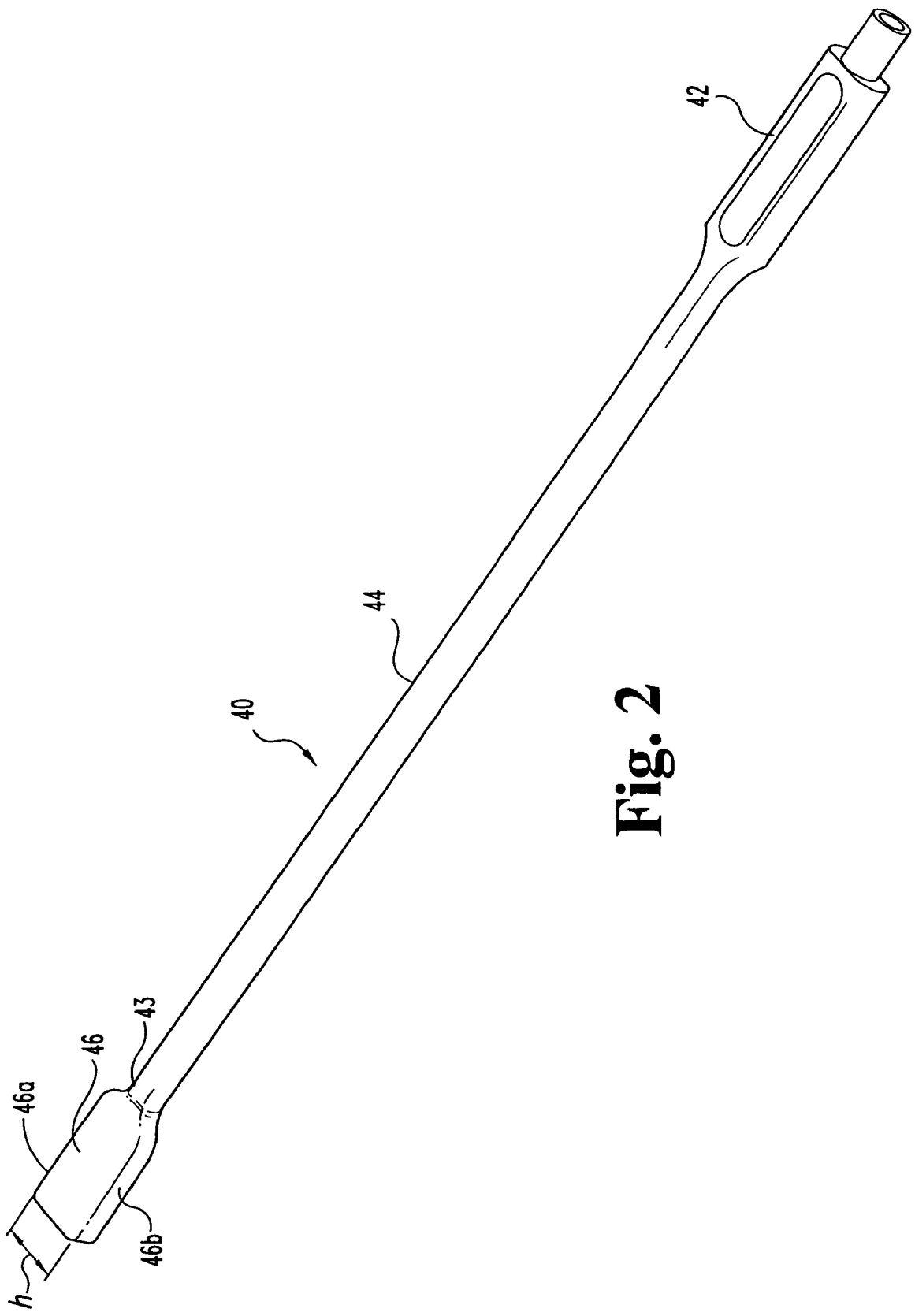
FIG. 2 is a perspective view of a distractor having application in the present invention.

In FIG. 2, a distractor 40 for distracting a disc space is provided. Distractor 40 includes a shaft 44 extending between a proximal end 42 and a distal end 43. Shaft 44 has a length sufficient to extend through cannula 20 with proximal end 42 disposed outside proximal end 22 of cannula 20. A head 46 extends from distal end 43. Head 46 is shown as integrally formed with shaft 44, but it is also contemplated that head 46 may be detachable via, for example, a threaded connection with shaft 44. Head 46 has a height h between support surfaces 46a and 46b that corresponds to the desired height for the distracted disc space. Proximal end 42 can be connected to a driving tool, such as a slap hammer or the like, to facilitate insertion. One example of a slap hammer is described hereinbelow with respect to FIG. 8. Distractor 40 may also be inserted by the surgeon by hand into the disc space.

It is contemplated that distractor 40 is inserted into the disc space support surface 46a and 46b transverse to the vertebral end plates, and distractor 40 is rotated to rotate head 46 so that support surfaces 46a and 46b contact a respective one of the vertebral endplates. It is also contemplated that a wrench or other tool configured to impart a rotational force to distractor 40 to rotate head 46 in the disc space can be connected at proximal end 42. It is further contemplated that a number of distractors 40 may be provided with varying heights h for sequential distraction of the disc space to the desired disc space height. The depth of insertion of blade 54 can be monitored under direct vision using viewing element 30. Also contemplated are x-ray imaging or image-guided navigation techniques that allow visualization of distractor 40 in the disc space. Instruments and techniques for image-guided navigation are further discussed in U.S. Pat. No. 6,021,343 to Foley et al. and also in PCT Application Serial No. PCT/US/95/12984 (Publication No. WO/96/11624) to Buchholz et al; each of which is incorporated herein by reference in its entirety.

Referring now to FIGS. 3(a) and 3(b), a shim 50 for maintaining distraction of a distracted disc space is provided. Shim 50 is extendable through cannula 20 to maintain distraction of a disc space distracted with distractor 40. Shim 50 includes a shaft 52 of sufficient length to extend through cannula 20 connected to a blade 54. Blade 54 has a first side surface 55a and a second side surface 55b. While blade 54 is shown as a flat blade, it is contemplated that any of a variety of blade shapes may be utilized in conjunction with shaft 52 of the present invention. Shaft 52 extends to proximal end 56. Shaft 52 has opposite side surface 53a and 53b that are co-planar with side surfaces 55a and 55b, respectively, of blade 54. Shaft 52 preferably is made from a material and has a configuration that allows shaft 52 to be bent away from axis A as needed to provide clearance for the surgeon to access the operative site through cannula 20.

Blade 54 has top surface 54a for contacting the superior vertebral endplate in the disc space and bottom surface 54b for contacting the inferior vertebral endplate in the disc space. Blade 54 has a leading end 60 extending between top surface 54a and bottom surface 54b. Preferably, leading end 60 is rounded to facilitate insertion of blade 54 into the disc space. Blade 54 also includes a pair of shoulders 62a and 62b. One shoulder 62a extends between shaft 52 and top surface 54a, and the other shoulder 62b extends between shaft 52 and bottom surface 54b. When blade 54 is inserted into the disc space, side surfaces 55a, 55b protect the disc space and prevent migration of tissue and other anatomical material laterally into the disc space during subsequent surgical procedures.

Blade 54 has a length l extending between leading end 60 and shoulders 62a, 62b. Preferably, length l is selected based on the depth of the disc space and the desired insertion depth of blade 54. Blade 54 also has a height h1 between top surface 54a and bottom surface 54b. Height h1 is preferably selected based on the height of the distracted disc space after it has been finally distracted with distractor 40. Blade 54 has a thickness t2 measured between first side surface 55a and second side surface 55b. It is contemplated that ratio of height h1 to thickness t1 is greater than about 2.0. In a most preferred form, this ratio is greater than about 5.0. Shaft 52 has a height h2, and a thickness t2 that preferably corresponds to blade thickness t1. However, it is also contemplated herein that thickness t1 and t2 have different values. It is preferred that height h1 of blade 54 is greater than height h2 of shaft 52.

In a specific embodiment of shim 50, blade 54 has thickness t1 of about 1.5 millimeters. Height h1 for the smallest sized blade 54 is 8.0 millimeters, and additional larger heights h1 are provided in increments of 2 millimeters. The shaft 52 in this specific embodiment has a height h2 of 6.0 millimeters and a thickness t2 of about 1.5 millimeters. Shim 50 is made from aluminum or other material that allows shaft 52 to be bent by the surgeon and maintained in the bent condition during surgery to effectively move the shaft out of the visual field.

Referring now to FIGS. 4(a)-4(c), a driver 70 for impacting or driving the shim 50 into the disc space is provided. Driver 70 includes a channel 72 and a handle 74 extending between a distal end 73 and a proximal end 76. Channel 72 is attached or formed at distal end 73 of handle 74 and extends distally therefrom. Driver 70 is particularly suited for use with shim 50 through cannula 20 because channel 72 is end-loaded over proximal end 56 of shaft 52. Preferably, channel 72 is offset from the handle 74, as shown in FIG. 4(b), to facilitate insertion of shaft 52 into channel 72 and manipulation of driver 70 with respect to shim 50.

Channel 72 has a wall 80 that extends therearound. Channel 72 has opposite end openings 78, 79 and a receptacle 73 defined by wall 80 that extends along the length of channel 72. Receptacle 73 is sized to slidably receive shaft 52 of shim 50 therein. Channel 72 includes a driving end 77 configured to contact shoulders 62a, 62b of shim 50, delivering the driving force at blade 54 without impacting shaft 52.

Use of driver 70 will now be described with respect to shim 50. Blade 54 is positioned at the desired insertion location adjacent the distracted disc space. The channel 72 is then end-loaded onto shaft 52 by placing opening 78 over proximal end 56. Driver 70 is slid along shaft 52 until driving end 77 is positioned adjacent blade 54. It is contemplated that a driving force can be provided to insert blade 54 into the disc space by withdrawing driver 70 a short distance away from shoulders 62a, 62b, and then applying a downward force so that driving end 77 impacts the shoulders 62a, 62b. This is repeated until blade 54 is inserted to the desired depth in the disc space. It is also contemplated that the driving force may be applied through driver 70 via a hammer or other device impacting driver 70. The depth of insertion of blade 54 can be monitored under direct vision using viewing element 30. Also contemplated are x-ray imaging or image-guided navigation techniques that allow visualization of blade 54 in the disc space. Thus, it is preferred that blade 54 be radiolucent.

A box chisel for preparation of a preformed cavity in the intervertebral disc space is depicted in FIGS. 5(a) and 5(b). Box chisel 90 includes a handle 92, having an engagement hole 93 adapted for attachment of an impacting tool such as a slap hammer or the like. It is also contemplated that chisel 90 can be manipulated by hand to form a cavity in the disc space. Box chisel 90 includes shaft 94 extending from handle 92 and connecting with cutting head 96. Shaft 94 defines a longitudinal axis 91 and has a length sufficient to extend through cannula 20. Cutting head 96 includes first arm 97 and opposing second arm 99 extending from shaft 94 substantially parallel to longitudinal axis 91. Upper cutting blade 98 and opposing lower cutting blade 100 are disposed between first and second arms 97 and 99. First arm 97 and second arm 99 define internal cavity 106 for receipt of bone chips and cutting debris. One or both of first arm 97 and second arm 99 include index markings 104, which indicate the depth of cut for the box chisel, thus allowing the surgeon to determine the depth of cut into the intervertebral space.

Non-cutting extension 103 is attached to first arm 97. Similarly, non-cutting extension 102 is attached to first arm 99. Non-cutting extensions 103 and 102 are positioned to extend distally beyond cutting blades 98 and 100 in a direction parallel to the longitudinal axis. Non-cutting extension 103 includes an upper guide surface 103a and a lower guide surface 103b extending at least partially distally beyond the cutting edges. Similarly, non-cutting extension 102 includes identical upper and lower guiding surfaces 102a and 102b. The guiding portions contact the surface of the adjacent vertebral endplates prior to cutting blades 98 and 100. Preferably non-cutting extensions 103 and 102 are rounded and follow the interior surfaces of the opposing end plates of adjacent vertebrae to center cutting blades 98 and 100 in the disc space between the two end plates. When the two cutting blades are centered between the opposing endplates, the blades generally cut equal amounts of bone from each end plate and are prevented from creating a potential offset opening between the endplates, resulting in improper implant placement and excess bone removal, which could increase the risk of implant interface subsidence.

Another embodiment of a chisel according to the present invention is curved chisel 110 depicted in FIGS. 6(a) and 6(b). Curved chisel 110 is for preparing a curved preformed cavity in the intervertebral disc space, and is particularly adapted for preparing a disc space for bi-lateral placement of implants in the disc space via a unitary transformational approach. Curved chisel 110 includes a handle 112, having an engagement hole 113 adapted for attachment of an impacting tool such as a slap hammer or the like. In addition, chisel 110 includes shaft 114 extending from handle 112 and connecting with cutting head 116. Shaft 114 defines a curvilinear longitudinal axis 111 having a radius of curvature R along a portion of its length. Radius R is provided such that chisel 110 may be inserted through the cannula 20 yet define a properly positioned and aligned cavity in the disc space. Cutting head 116 includes first arm 117 and opposing second arm 119 extending from shaft 114 substantially parallel to longitudinal axis 111. Upper cutting blade 118 and opposing lower cutting blade 120 are disposed between first and second arms 117 and 119. First arm 117 and second arm 119 define internal cavity 126 for holding bone chips and cutting debris passed rearwardly from cutting head 116.

Non-cutting extension 123 is attached to first arm 117. Similarly, non-cutting extension 122 is attached to first arm 119. Non-cutting extensions 123 and 122 are positioned to extend distally beyond cutting blades 118 and 120 in a direction parallel to the longitudinal axis. Non-cutting extension 123 includes an upper guide surface 123a and a lower guide surface 123b extending at least partially distally beyond the cutting edges. Similarly, non-cutting extension 122 includes upper and lower guiding surfaces 122a and 122b. The guiding surfaces contact the vertebral endplates prior to cutting blades 118 and 120. Preferably non-cutting extensions 123 and 122 are rounded and follow the interior surfaces of the opposing end plates of adjacent vertebrae to center cutting blades 118 and 120 in the disc space between the two end plates. When the two cutting blades are centered between the opposing endplates, the blades cut equal amounts of bone from each end plate and are prevented from creating a potential offset opening between the endplates, resulting in improper implant placement and excess bone removal, which could increase the risk of implant interface subsidence.

In use chisels 90, 110 are positioned through cannula 20 with viewing element 30 connected thereto. Cutting heads 96, 116 are positioned in substantial alignment with a disc space between adjacent vertebral endplates under direct vision. Non-cutting edges are inserted into the disc space with the guide surfaces of extensions 102, 103 of chisel 90 or guide surfaces of extensions 122, 123 of chisel 110 contacting the vertebral endplates. Cutting head 96, 116 is then advanced, by hand or by use of a slap hammer if necessary, with blades 98, 100 of chisel 90 or blades 118, 120 of chisel 110 removing the tissue of the vertebral endplates along the path of insertion. The depth of insertion of chisels 90, 110 can be monitored under direct vision, image-guided navigation instruments, with a viewing element inserted in the disc space, or via x-ray or fluoroscopic imaging A distractor-cutter instrument is described hereinbelow and also in U.S. patent application Ser. No. 09/692,980; entitled METHODS AND INSTRUMENTS FOR INTER-BODY SURGICAL TECHNIQUES, filed Oct. 20, 2000, which application is incorporated herein by reference in its entirety. Referring now further to FIGS. 7(a)-7(d), there is shown a distractor assembly 210 that includes a distractor 218 at the distal end of stem 216. At the proximal end of stem 216 is a coupling 214 for securing handle 212 to stem 216. Distractor 218 includes a body portion 220 extending between leading end 222 and trailing end 224. A first flange 226 and a second flange 228 are secured to body portion 220 at leading end 222, and extend from leading end 222 towards trailing end 224. It is preferred that flanges 226, 228 are integrally formed with body portion 220 at leading end 222. In the illustrated embodiment, a first end wall 246 extends between leading end 222 and first flange 226 and a second end wall 248 extends between leading end 222 and second flange 228. However, flanges 226, 228 could also be removably attached to body portion 220.

Body portion 220 has first sidewall 230 and an opposite second sidewall 232. Each of the sidewalls 230, 232 extend towards the adjacent vertebrae between an upper surface 234 and an opposite lower surface 236 of body portion 220. A first slot 242 is formed between first flange 226 and first sidewall 230. A second slot 244 is formed between second flange 228 and second sidewall 232. Slots 242 and 244 have a width "d" sized to accommodate the distal end of a cutting instrument 252, as discussed further below.

Body portion 220 further includes a cavity 238 formed therethrough extending between upper surface 234 and the opposite lower surface. Body portion 220 has a height H1 between upper surface 234 and lower surface 236 that corresponds to the desired height for the distracted disc space. In the illustrated embodiment, the leading end portion of body portion 220 tapers to a reduced height H2 between upper surface 234 and lower surface 236 at leading end 222 to facilitate insertion of distractor 218 into the disc space. Preferably, flanges 226, 228 have a height that is equal to or is less than height H1 of body portion 220, and have a tapered portion that corresponds to the taper of body portion 220 towards leading end 222. The depth of insertion of distractor 218 into the disc space can be monitored under direct vision, image-guided navigation instruments, with a viewing element inserted in the disc space, or via x-ray or fluoroscopic imaging of distractor 218.

According to a further aspect of the invention a cutting instrument or cutter 252 is provided that cooperates with distractor 218 to form a spinal instrument assembly 250. Spinal instrument assembly 250 provides for distraction of the adjacent vertebrae and for cutting material from the disc space and/or the adjacent vertebrae to form an implant insertion location. Cutter 252 includes a shaft 264 and a cutting head 253 at the distal end of shaft 264. Shaft 264 includes a first sidewall 258 and an opposite sidewall 260. Sidewalls 258 and 260 are connected by an upper member 254 and an opposite lower member 256. Upper member 254 includes an upper cutting edge 254a at its distal end and lower member 256 includes a lower cutting edge 256a at its distal end. While the illustrated embodiment has shaft 264 with a square cross-sectional shape, other shapes are also contemplated, including, for example, a circular or rectangular cross-section.

Figure 7A:
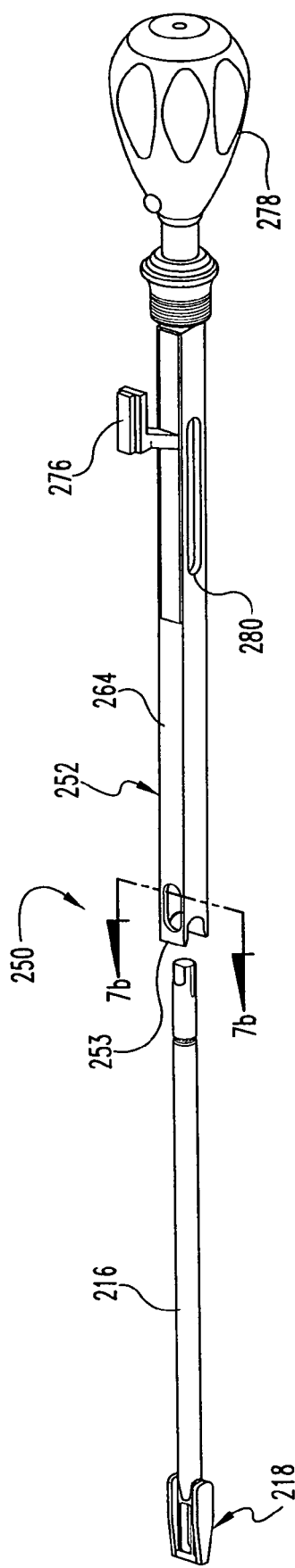
FIG. 7(a) is a perspective view of a distractor-cutter assembly according to a further aspect of the present invention.
Figure 7B:
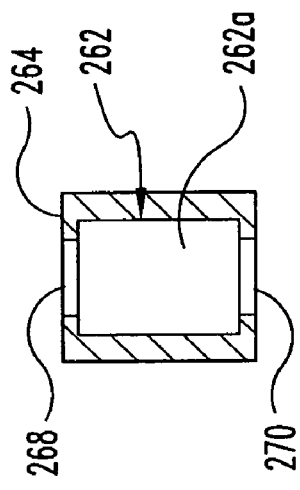
FIG. 7(b) is a sectional view taken through line 7(b)-7(b) of FIG. 7(a).
Figure 7C:
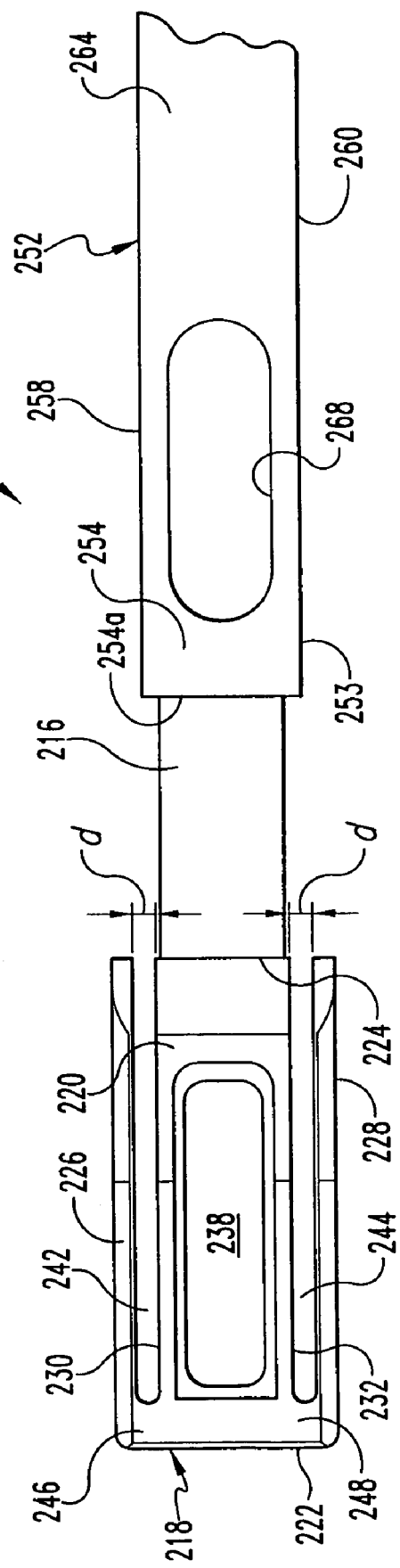
FIG. 7(c) is an enlarged top plan view of the distal end portion of the distractor-cutter assembly of FIG. 7(a).
Figure 7D:
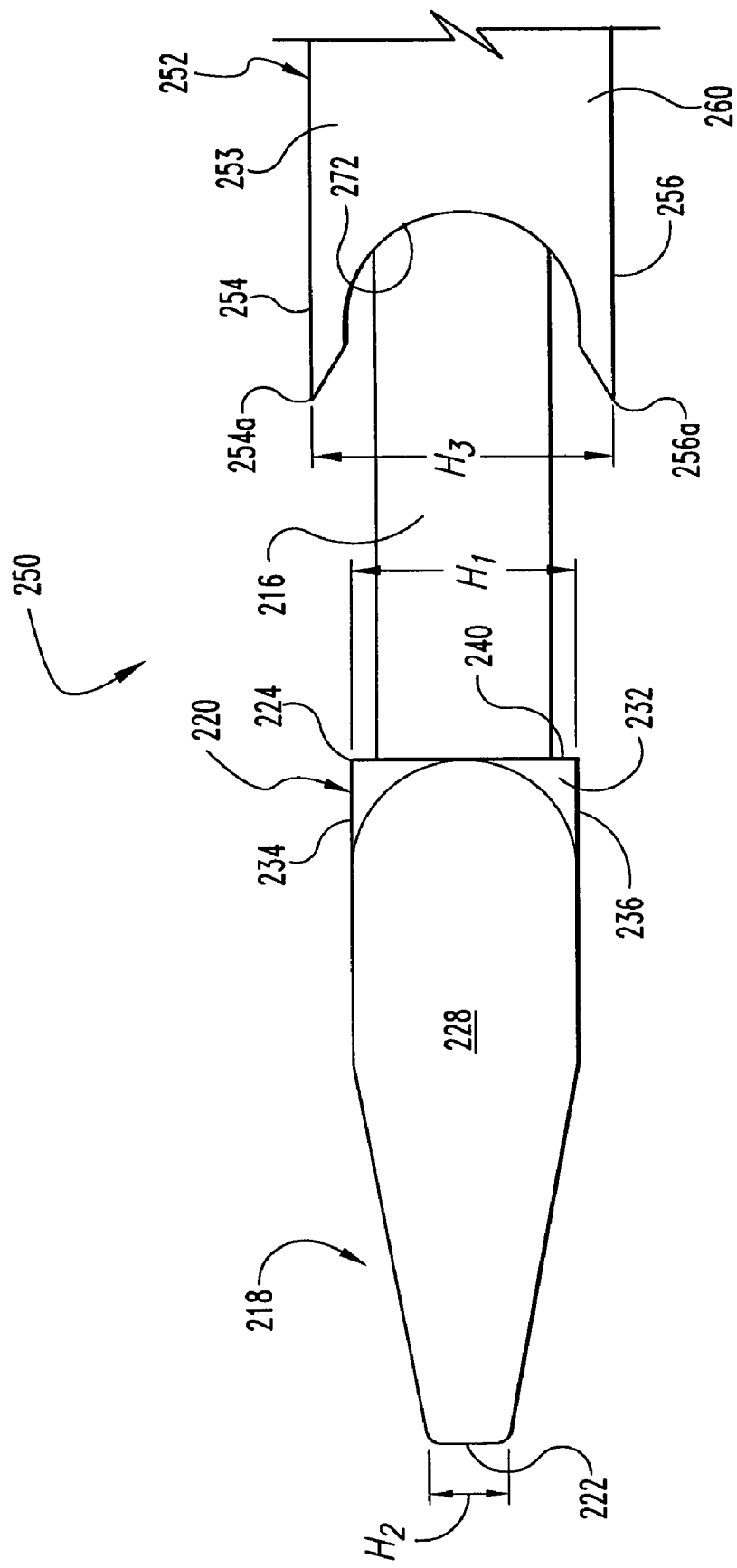
FIG. 7(d) is an enlarged side elevation view of the distal end portion of the distractor-cutter assembly of FIG. 7(a).

Shaft 264 includes an interior channel 262 formed therethrough that opens at the distal end of cutter 252. As shown in FIG. 7(b), channel 262 has a distal first portion 262a sized to receive stem 216 and body portion 220 of distractor assembly 210 with handle 212 removed from stem 216. Preferably, first portion 262a has a size slightly larger than body portion 220 and a shape approximating the shape of body portion 220. This provides a slip fit between body portion 220 and cutting head 253 that will guide cutting head 253 into the disc space and into the bony material of the adjacent vertebral bodies. Although the cross-section of the remaining proximal portion of channel 262 can have any shape, it is contemplated that the entire length of channel 262 has a shape that corresponds to the shape of first portion 262a.

Upper member 254 includes an opening 268 and lower member 256 includes an opening 270 identical to opening 268. These openings are substantially alignable with cavity 238 of distractor 218, and facilitate the removal of cut material from cavity 238 when instrument assembly is withdrawn from the disc space after cutting bony material. Cutter sidewall 260 includes a recess 272 formed therein, and cutter sidewall 258 includes a similarly shaped recess (not shown.) The recesses allow cutting edges 254a and 256a to be advanced beyond the leading end 222 of distractor 218. End walls 246, 248 prevent cutting head 253 from being advanced too far beyond leading end 222 of body portion 220.

Sidewall 260 includes a window 280 to further provide visual observation and/or confirmation of the position of cutting head 253 with respect to distractor 218 by enabling viewing of depth markings on stem 216 of distractor assembly 210. Shaft 264 further includes a probe 274 for image guided navigation adjacent its proximal end to provide control and monitoring of cutter 252. Further details regarding probe 274 are provided in U.S. Pat. No. 6,021,343 to Foley et al. Also contemplated are the use of x-ray and fluoroscopic imaging techniques to visualize cutting head 253 as it is inserted in the disc space.

Head 246 has a height H3 that corresponds to the desired height of the prepared disc space into which the implant is to be inserted. It is contemplated that cutter 252 is inserted into the disc space with upper member 254 and lower member 256 parallel to the vertebral end plates and guided by body portion 220 of distractor 218. It is further contemplated that a number of cutters 252 of increasing height H3 may be provided and sequentially inserted over distractor 218 for removal of bony material from the vertebral endplates. A standard coupling 76 is provided at the proximal end of cutter 252 for attachment to a cutter handle 278 to facilitate gripping and control of cutter 252. The proximal end of cutter 252 can also be connected to or contacted by a driving tool, such as a slap hammer or the like to drive the cutting edges 254a, 256a into the bony material.

Figure 8:
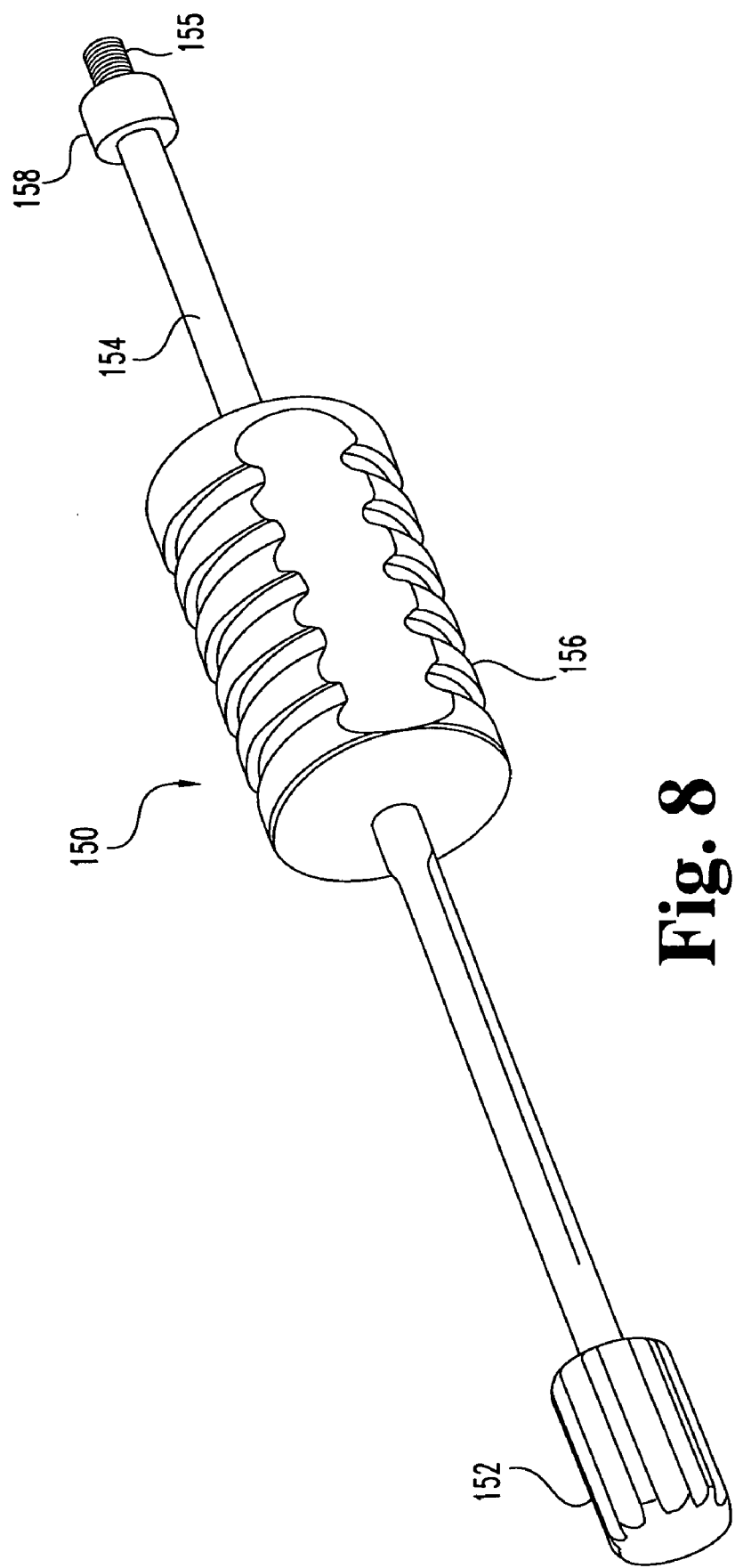
FIG. 8 is a perspective view of a slap hammer having application with the present invention.
Figure 9:
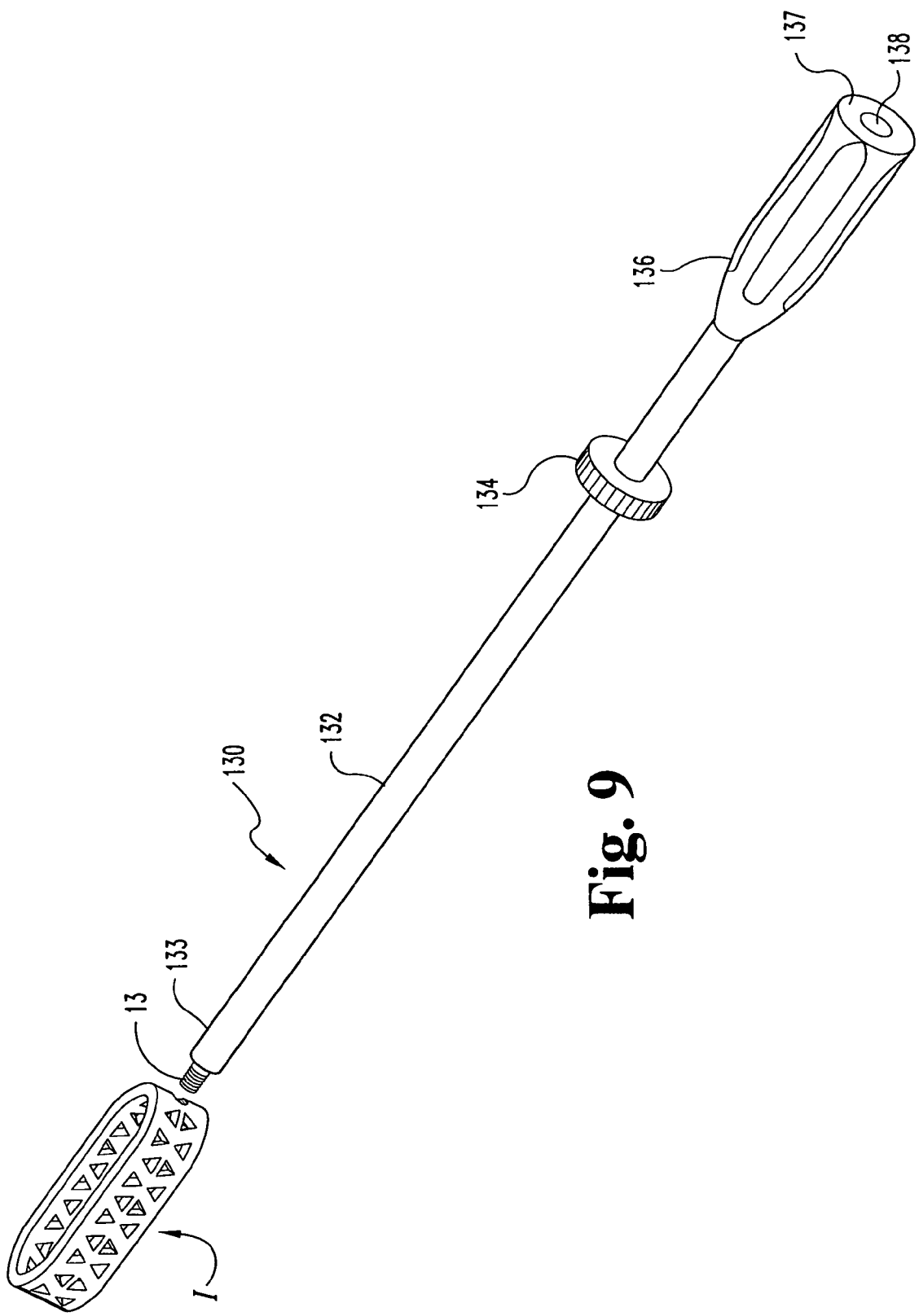
FIG. 9 is a perspective view of an implant holder and implant having application with the present invention.

FIG. 8 shows one example of a slap hammer engageable to attachment hole 93 of box chisel 90, to attachment hole 113 of chisel 110, to cutter 252, to distractor assembly 210 or implant holder 130 (FIG. 9.) Slap hammer 150 includes handle 152 and a shaft 154 extending to an opposite threaded end 155. Threaded end 155 threadedly engages internal threads in holes 93, 113. Slap hammer 150 includes weight 156 that slides along shaft 154. Slap hammer 150 allows for controlled force when impacting the connected instrument. The slap hammer also provides a means for removal of impacted surgical tools from the disc space.

Referring now to FIG. 9, an embodiment of an implant holder 130 and an interbody fusion device, such as implant I, are illustrated. The implant holder 130 includes a shaft 132 extending between a handle 136 and distal end 133. Shaft 132 has a length sufficient to extend through cannula 20. Implant holder 130 releasably secures an implant for insertion into a preformed cavity in the disc space under direct vision with viewing element 30. Distal end 133 includes threaded extension 135 threadedly received within an internally threaded opening in implant I in order to engages implant holder 130 thereto. Handle 136 includes a proximal end 137 that may be impacted in order to insert the implant in the disc space. In one embodiment, proximal end 137 includes internally threaded opening 138 configured to engage slap hammer 150. The surgeon may also insert implant I into the disc space by hand using handle 136. In addition to the visualization techniques described herein or those known in the art, an adjustable depth stop 134 may be provided on shaft 132 to control the depth of insertion of implant I into the disc space. Once implant I has been driven into the disc space, the implant is released from implant holder 130.

Implant I may be any device suitable for insertion into the disc space through cannula 20. Use of implants that restore the disc height, restore segmental alignment and balance, protect nerve roots, restore weight bearing to anterior surfaces, and immobilize the unstable degenerated intervertebral disc area are contemplated. The implants inserted with the techniques of the present invention may be conveniently implanted using the instruments and tools of the present invention to prepare the disc space and any instrument that will firmly hold implant I and permit insertion in the disc space through cannula 20 is also contemplated.

Implant I can be a spacer or interbody fusion device. Implant I may have an oblong cross-section, as shown in FIG. 9, or have a cross-section that is circular, oval, square, trapezoidal or rectangular. Implant I may be sized such that a single implant I is inserted in the disc space, or may have a size so that two or more implants can be inserted and bi-laterally positioned in the disc space. Examples implants I in the form of an interbody fusion devices are described in U.S. Pat. No. 5,897,556 which is incorporated herein by reference. Other examples of suitable interbody fusion devices are described in Provisional Application Ser. No. 60/160,506 filed on Oct. 20, 1999, which application is incorporated herein by reference in its entirety. In yet another example, a banana-shaped implant is inserted in to the disc space. An example of such a banana-shaped implant is disclosed in Provisional Application Ser. No. 60/160,667 filed on Oct. 21, 1999, which application is incorporated herein by reference in its entirety.

Figure 12:
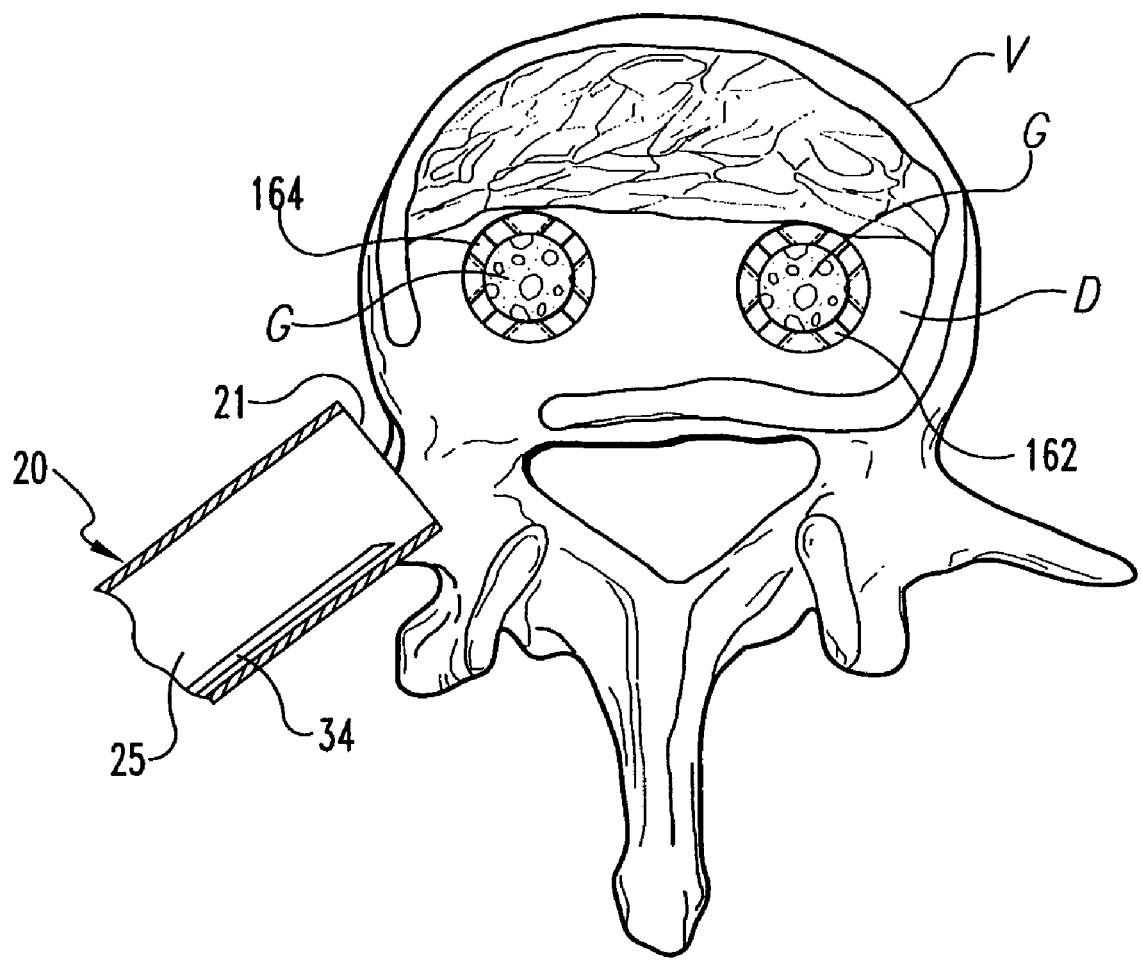
FIG. 12 is a plan view of a disc space illustrating bi-lateral positioning of interbody fusion devices in the disc space.

It is preferred that the interbody fusion devices inserted into the disc space have a hollow interior forming a chamber or depot for osteogenic or bone-growth material G (FIG. 12.) The device can be packed with osteogenic material prior to implantation in the disc space, or the osteogenic material may be inserted into the chamber or depot after one or more of the devices have been inserted. In a preferred embodiment, the osteogenic composition substantially fills the hollow interior defined by the devices to promote fusion and bone growth between the adjacent vertebrae. It is also contemplated that osteogenic or bone growth material may be packed around the device(s) in the disc space.

Any suitable osteogenic material or composition is contemplated, including autograft, allograft, xenograft, demineralized bone, and synthetic and natural bone graft substitutes, such as bioceramics and polymers, and osteoinductive factors. The terms osteogenic material or osteogenic composition used herein broadly include any material that promotes bone growth or healing including autograft, allograft, xenograft, bone graft substitutes and natural, synthetic and recombinant proteins, hormones and the like.

The steps of the spinal surgical procedure in accordance with one aspect of the present invention are depicted in FIGS. 10(a)-10(h). As can be discerned from each of the depicted steps (a)-(h), the present invention contemplates a transformational approach to the disc space, as indicated by cannula 20. The following surgical steps also have application with other approaches to the spine, such as the medial posterior approach indicated by cannula 20', or other posterior, postero-lateral and anterior approaches. In the discussion that follows, reference will generally be made to a transformational approach.

In a first step of the technique, a guidewire 170 can be advanced through the skin and tissue into the facet joint of a vertebral body V. A small incision can be made in the skin to facilitate penetration of guidewire 170 through the skin. In addition, the guidewire, which may be a K-wire, can be inserted under radiographic or image guided control to verify its proper positioning on the vertebra V. The positioning of the guidewire is dependent upon the surgical procedure to be conducted through the working channel cannula of the present invention. Preferably, the guidewire 170 is solidly anchored into the vertebral bone, being tapped by a mallet if necessary.

In subsequent steps of the preferred method, a series of tissue dilators are advanced over the guidewire 170, as depicted in FIGS. 10(b)-10(d). Alternatively, the dilators can be advanced through the incision without the aid of a guidewire, followed by blunt dissection of the underlying tissues. In the specific illustrated embodiment, a series of successively larger dilators 171, 172 and 173 are concentrically disposed over each other and over the guidewire 170 and advanced into the body to sequentially dilate the soft tissues. In a specific embodiment, the dilators have successively larger diameters, with sizes that increase from the smallest to the largest dilator depending upon the anatomical approach and upon the desired size of the working channel for cannula 20.

In the next step of the illustrated technique, the working channel cannula 20 is advanced over the largest dilator 173, as shown in FIG. 10(e), and the dilators and guidewire 170 are removed, as shown in FIG. 10(f). Preferably, the working channel cannula 20 has an inner diameter such that it can be easily advanced over the outer diameter of the large dilator 173. Cannulas having various sized working channels are contemplated depending upon the anatomical region and surgical procedure.

With the cannula 20 in position, a working channel is formed between the skin of the patient to a working space adjacent the spine. It is understood that the length of the cannula 20 is determined by the particular surgical operation being performed and the anatomy surrounding the working space. For instance, in the lumbar spine the patient requires a longer cannula 20 than a similar procedure performed in the cervical spine where the vertebral body is generally closer to the skin.

In accordance with the present surgical technique, the working channel cannula 20 is at least initially only supported by the soft tissue and skin of the patient. Thus, in one aspect of the preferred embodiment, the cannula 20 can include a mounting bracket 27 affixed to the outer surface of the cannula (FIG. 10(f)). This mounting bracket 27 can be fastened to a table-based flexible support arm 160, which can be of known design. Preferably, the flexible support arm 160 is engaged to the bracket 27 by way of a bolt and wing nut 161, as shown in FIG. 10(h), although other fasteners are also contemplated. This flexible arm 160 can be mounted to the surgical table and can be readily adjusted into a fixed position to provide firm support for the cannula 20. The flexible arm 160 preferably may be contoured as required to stay clear of the surgical site and to allow the surgeons adequate room to manipulate the variety of tools that would be used throughout the procedure. Returning to FIG. 10(g), once the cannula 20 is seated within the patient, endoscope assembly 30 can be engaged over the proximal end of the cannula 20. Endoscope assembly 30, as shown in FIG. 1 and described above, provides an endoscope with an elongated viewing element, such as element 34 in FIG. 1, that extends through cannula 20 adjacent the working channel.

With the endoscope assembly 30 supported by cannula 20, the surgeon can directly visualize the area beneath the working channel 25 of the cannula 20. The surgeon can freely manipulate the viewing element 34 within the working channel 25 or beyond the distal end of the cannula into the working space. In the case of a steerable tip scope, the second end 34a of viewing element 30, which carries the lens, can be manipulated to different positions. With virtually any type of viewing element, the manipulation and positioning of the scope is not limited by the procedure to be performed. For instance, variety of rongeurs, curettes, trephines, distractors, distractor-cutters, chisels, shims, and implant holders can be extended through working channel 25 of cannula 20 (see FIG. 1) into the working space. It is understood that these various tools and instruments are designed to fit through the working channel. The present invention is not limited to particular sizes for the working channel and effective diameter, since the dimensions of the components will depend upon the anatomy of the surgical site and the type of procedure being performed.

One important feature of the present invention is achieved by the large diameter of the working channel 25 in the cannula 20. This large diameter allows the surgeon or surgeons conducting the surgical procedure to introduce a plurality of instruments or tools into the working space. For example, as described above, a distractor and a shim, a chisel and a shim, a distractor-cutter or a distractor-cutter and a shim, or an implant and a shim could be extended together through the working channel. Likewise, the present invention contemplates the simultaneous introduction of other types of instruments or tools as may be dictated by the particular surgical procedure to be performed. For example, discectomy instruments could be inserted through channel 25, such as a trephine for boring a hole through the disc annulus and a powered tissue cutter for excising the herniated disc nucleus. An appropriately sized curette and a rongeur may be simultaneously extended through the working channel into the working space. Since all operations being conducted in the working space are under direct visualization through the viewing element, the surgeon can readily manipulate each of the instruments to perform tissue removal and bone cutting operations, without having to remove one tool and insert the other. Furthermore, aspects of the invention which permit a wide range of motion to the viewing element allow the surgeon to clearly visualize the target tissue and clearly observe the surgical procedures being conducted in the working space.

The surgeon can capitalize on the same advantages in conducting a wide range of procedures at a wide range of locations in the human body. For example, a facetectomy could be conducted through the working channel by simply orienting the working channel cannula 20 over the particular facet joints. The devices can also be used to prepare a site for fusion of two adjacent vertebrae, and for implantation of a fusion device or material.

For example, one surgical technique will now be described with reference to FIGS. 11(a)-11(h). Those skilled in the art will understand the FIGS. 11(a)-11(h) demonstrate a transformational approach to the disc space that requires removal of the facet joint to provide access to the disc space in an oblique orientation relative to the midline of the vertebral bodies. This approach allows disc space preparation and insertion of one or more implants bilaterally into the disc space via a unitary approach to the disc space.

An incision can be made in the skin posterior to a particular disc space to be fused. As the tissue beneath the skin is successively excised or retracted, the working channel cannula 20 can be progressively advanced toward the anticipated working space adjacent the vertebral disc and secured with flexible arm 160, as shown in FIGS. 10(a)-10(h). Endoscope assembly 30 is then mounted on cannula 20, and the remaining steps of the procedure can be performed under direct vision from viewing element 34. A portion of the facet joints of the adjacent vertebral bodies are resected through cannula 20, and a discectomy is performed through cannula 20. Typically, this preparation includes preparing an opening in the disc annulus, and excising all, or preferably as part, of the disc nucleus through this opening. If a partial discectomy is performed, enough material is removed to allow insertion of the distractor.

Figure 11A:
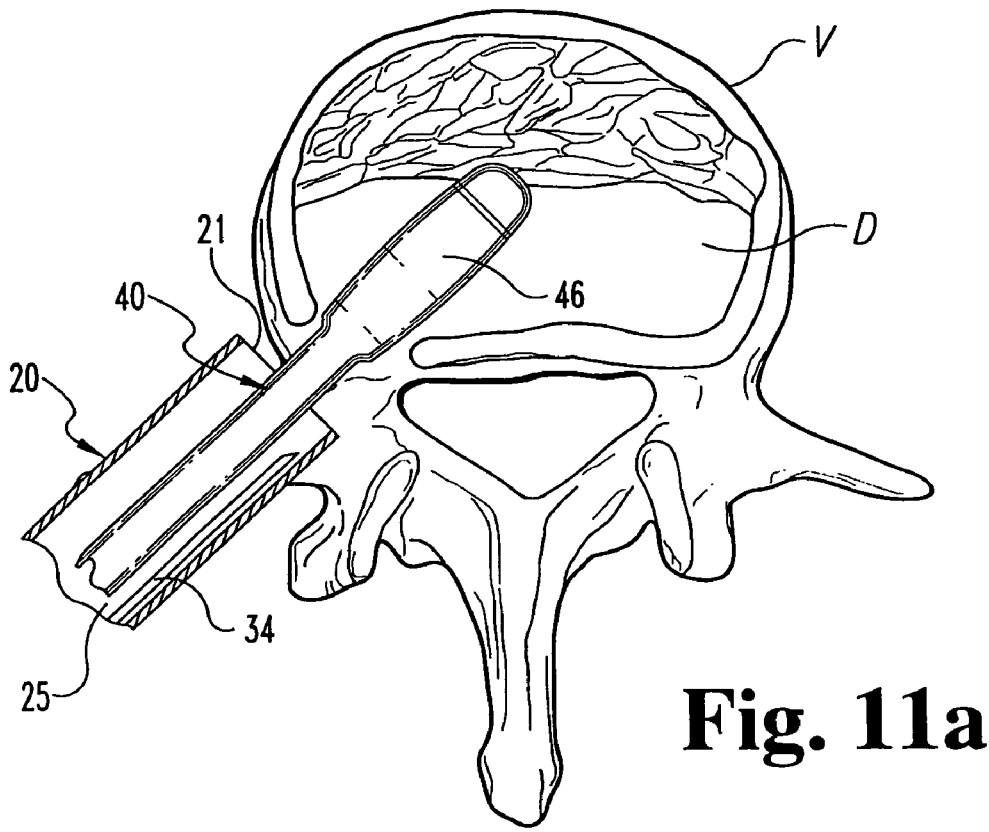
FIGS. 11(a)-(h) depict the steps of a method for preparing a disc space for insertion of interbody fusion device into a disc space.
Figure 11B:
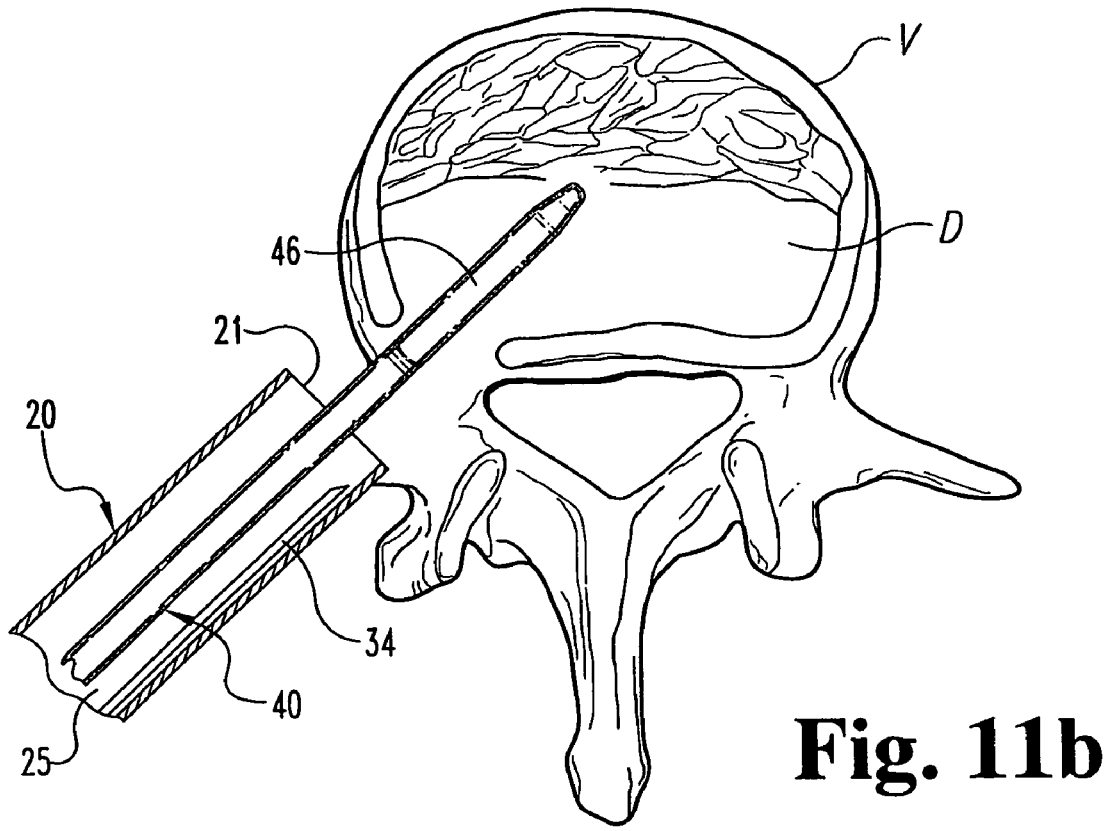
Figure 11C:
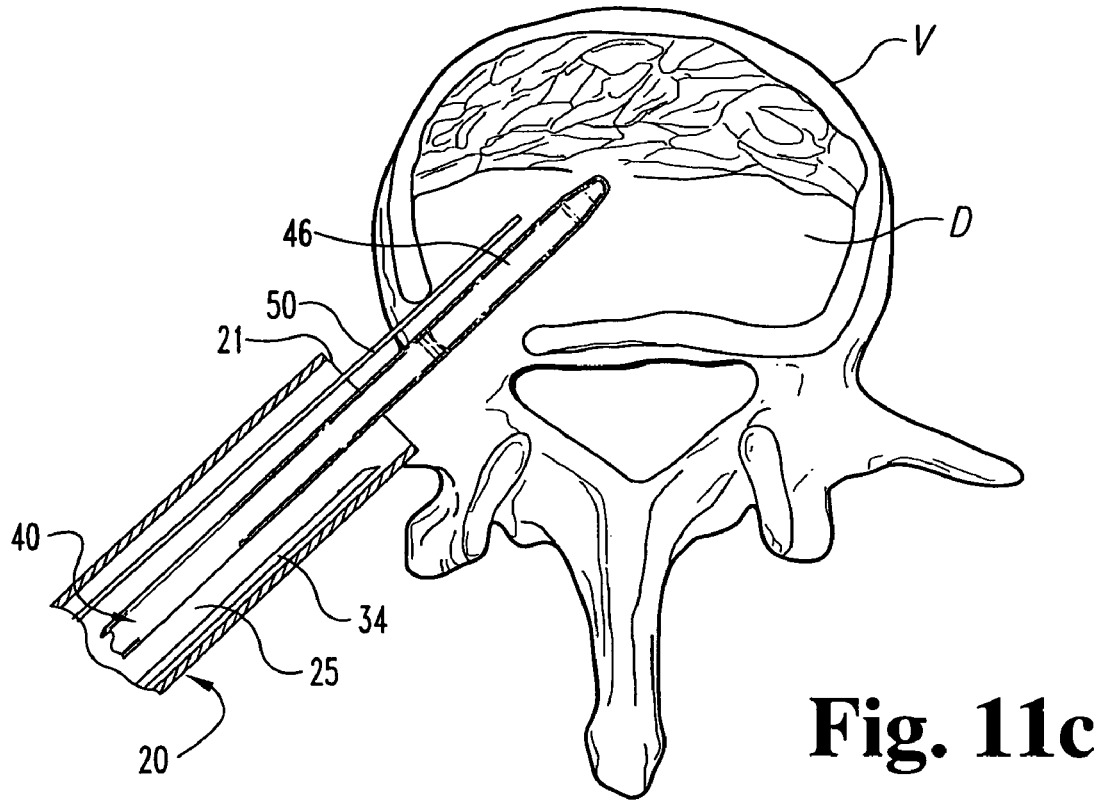

In subsequent steps, the disc space is distracted to the desired disc space height. As shown in FIG. 11(a) distractor 40 is inserted through cannula 20 into the disc space. The disc space is distracted with distractor 40 by rotating head 46 ninety degrees in the disc space, as shown in FIG. 11(b). The disc space can be sequentially distracted until the desired disc space height is obtained. To sequentially distract the disc space, shim 50 is inserted into the disc space adjacent distractor 40, as shown in FIG. 11(c), to maintain the distracted disc space height after removal of distractor 40. Preferably, driver 70 is used to drive shim 50 to the desired depth. If necessary, the first distractor is removed and a next larger distractor 40 is inserted into the disc space, and the first shim removed. Another shim 50 corresponding to the next larger distractor height is then inserted as described above. When the desired disc space distraction has been achieved, the final distractor is removed from the disc space, and disc space preparation continues adjacent shim 50 that remains in the disc space. In addition to maintaining distraction of the disc space, shim 50 also shields the disc space and helps prevent migration of nerves and tissue into the working space. The bendable shaft of shim 50 can be bent over the proximal end of cannula 20 to provide clear access to working channel 25. A complete discectomy, if necessary, can now be completed while the shim supports the disc space in an open position.

Figure 11D:
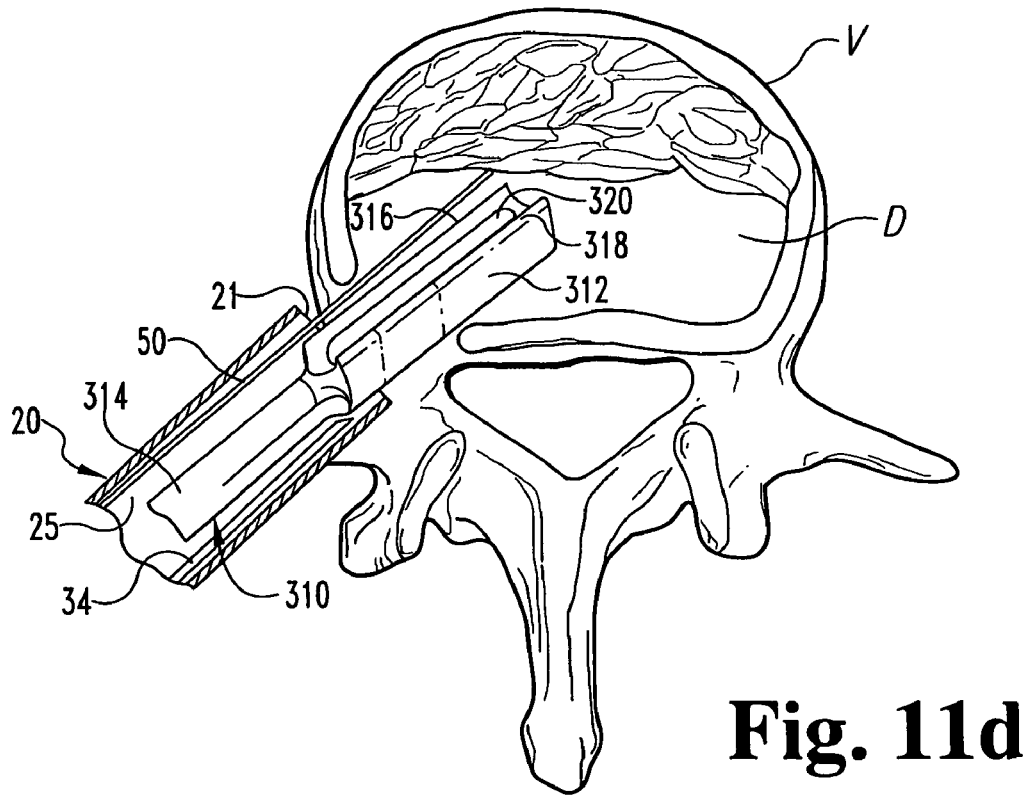

As shown in FIG. 11(d), it is contemplated that one type of instrument that could be inserted through working channel 25 of cannula 20 to complete the discectomy is a rotate cutter 310, such as the rotate cutter described in U.S. patent application Ser. No. 09/181,353, which is incorporated herein by reference in its entirety. The rotate cutter 310 has a head 312 inserted alongside the shim and rotated by a shaft 314 once or twice to remove residual disc material and osteophytes at the dorsal-most endplate. Blades 316, 318 cut the disc material and deposit it in trough 320 between blades 316, 318 for removal from the disc space. Removal of osteophytes facilitates placement of the chisel 90, 110 in the disc space. Sequentially larger rotate cutters can be inserted to remove disc material safely.

Figure 11E:
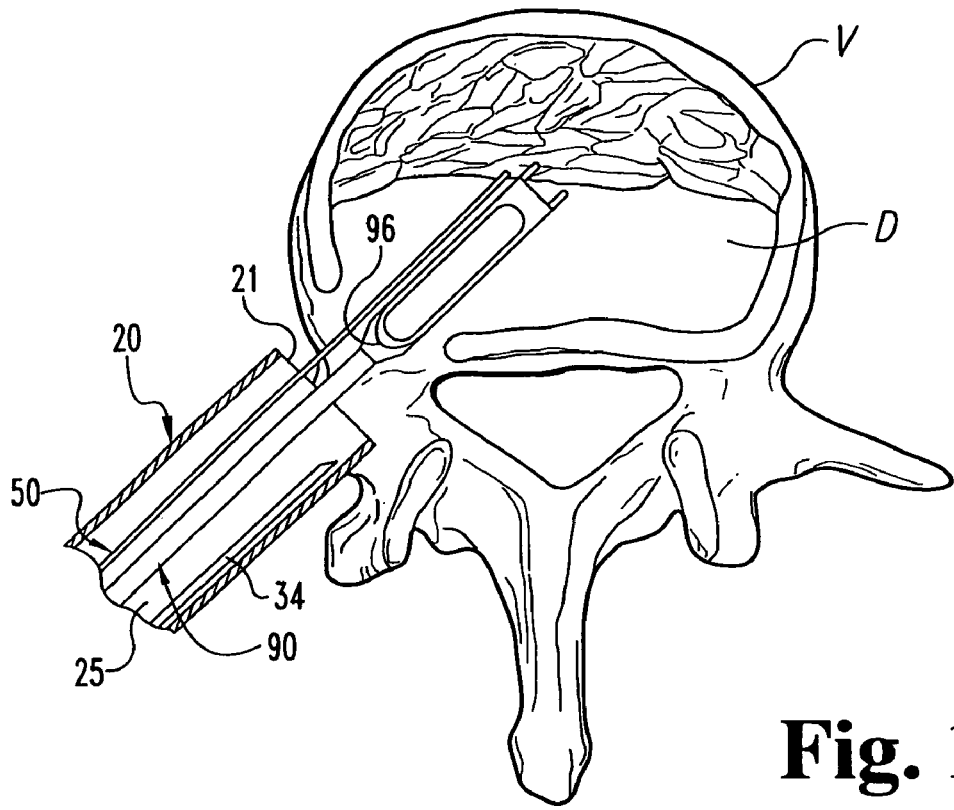
Figure 11F:
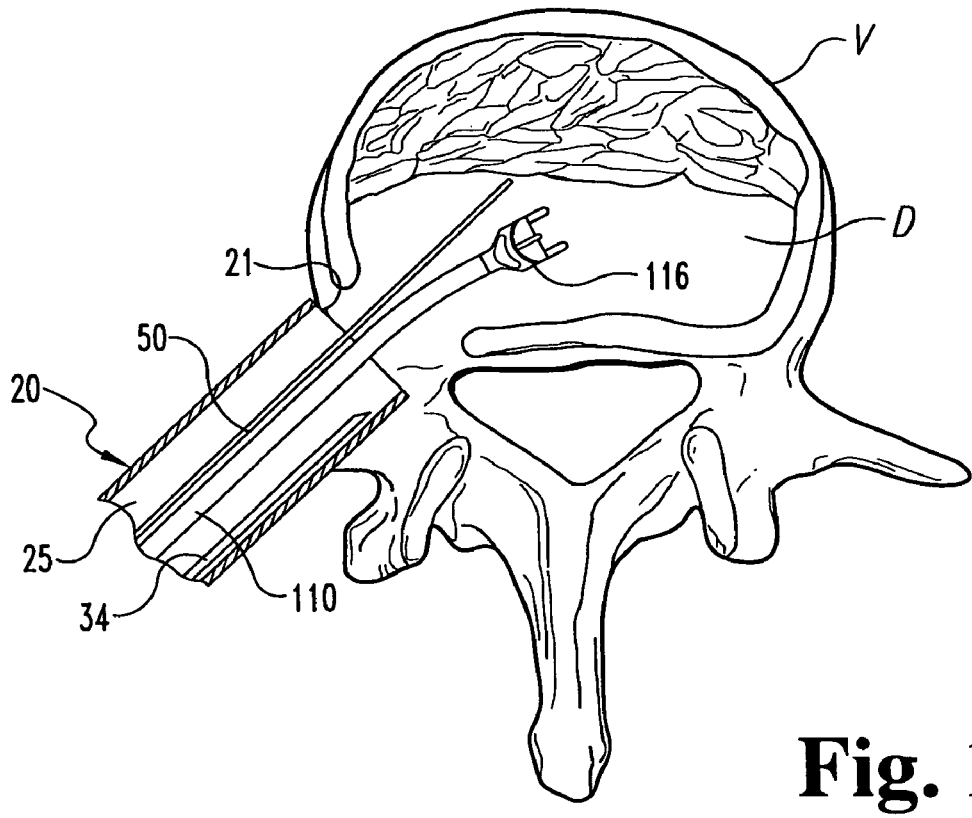

As shown in FIGS. 11(e) and 11(f), box chisel 90 or curved chisel 110 is next used to form an insertion location for one or more implants, depending on the patient anatomy and desired positions of the one or more implants. Chisel 90, 110 are inserted through cannula 20 to cut the endplates of the adjacent vertebrae to form a cavity or trac for implant insertion while shim 50 maintains disc space distraction. If necessary, cannula 20 can be manipulated through the skin and tissue to provide different cutting angles with respect to the disc space for further bone removal. After removal of the chisel 90, 110 the discectomy rongeur and other instruments can be inserted through cannula 20 to remove any residual soft tissue and bone material.

Figure 11G:
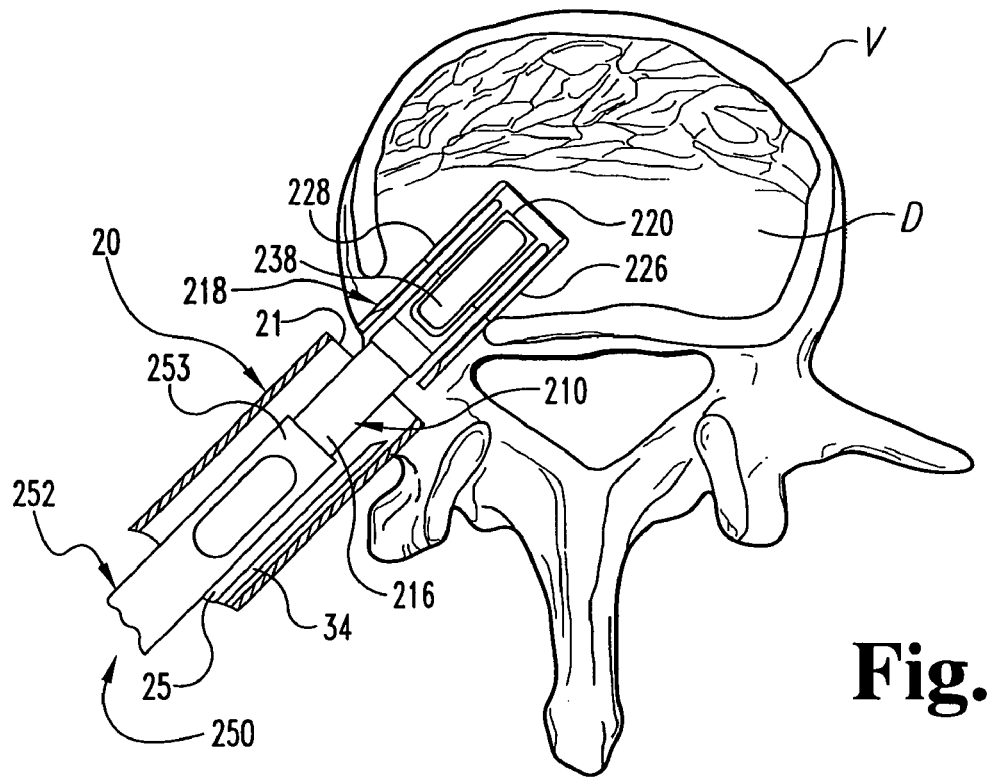

As shown in FIG. 11(g), distractor-cutter 250 can be used in addition to or as an alternative distractor 40 and chisel 90. Distractor assembly 210 is inserted into disc space D through working channel 25 of cannula 20 to distract disc space to the desired height between the adjacent vertebrae. It is contemplated that, if necessary, the disc space can be sequentially distracted before insertion of distractor 218 or sequentially distracted by a number of distractors 218 of increasing height H1 until the desired disc space height is obtained.

When the desired distraction has been achieved, handle 212 is removed from the proximal end of stem 216 and cutter 252 is slid over the proximal end of stem 216 to position cutting head 253 adjacent the disc space and distractor 218. Cutter 252 is advanced over body portion 220 of distractor 218 so that the bony material of the vertebral endplates is cut by cutting edges 254a and 256a. At least a portion of the cut material is deposited in cavity 238 of distractor 218. Cutter 252 forms a path or trac for implant insertion while distractor 218 maintains disc space distraction. If necessary, cannula 20 can be manipulated through the skin and tissue to provide different cutting angles with respect to the disc space for further bone removal. Flanges 226, 228 protect the adjacent vasculature and nerves as cutter 252 advances over body portion 220, and body portion 218 guides the cutting edges to provide a uniform and controlled depth of cut and bone removal of the adjacent vertebral bodies.

Figure 11H:
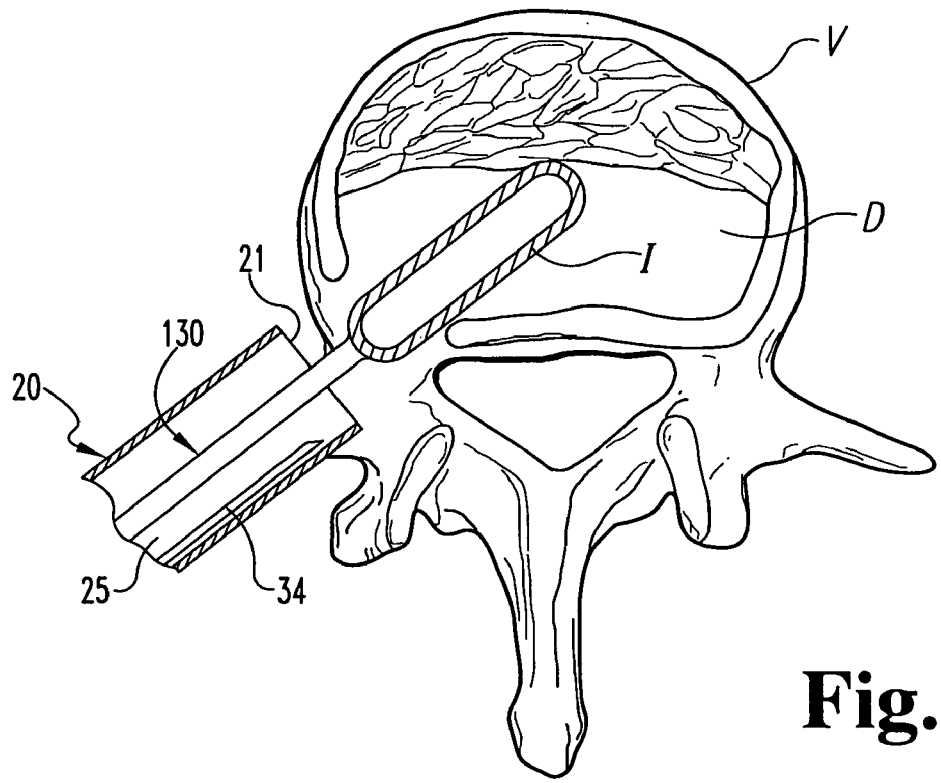

Implant I, preferably a fusion device, bone dowel, push-in implant, threaded implant or the like, can then be advanced through the working channel 25 of cannula 20 and into the prepared cavity or trac at the subject disc space via implant holder 130. The depth of insertion can be controlled via depth stop 134. The implant I of FIG. 11(h) is elongated, and provides bi-lateral support of the vertebral bodies. It is also contemplated that more than one implant can be inserted into the disc space, as shown in FIG. 12. The first interbody fusion device 162 is positioned at a first bi-lateral location in the disc space opposite cannula 20. A second interbody fusion device 164 can then be positioned at a second bi-lateral location in the disc space. First and second devices 162, 164 provide bilateral support of the adjacent vertebrae, and can be packed with bone growth material G.

In some instances, the preparatory steps involve preparing the vertebral endplates by reducing the endplates to bleeding bone. In this instance, some aspiration and irrigation may be beneficial. The above procedures can be conducted by tools and instruments extending through working channel cannula 20 and under direct vision from endoscope assembly 30. Graft material may also be placed directly in the prepared bore in the disc space, either without any interbody fusion device or packed around the inserted devices. This graft material can also be passed through the working channel cannula 20 into the disc space location.

While the invention has been illustrated and described in detail in the drawings and the foregoing description, the same is considered to be illustrative and not restrictive in character. It is understood that only the preferred embodiments have been shown and described and that all changes and modifications that come within the spirit of the invention are desired to be protected.

What is claimed is:

1. A method for inserting at least one interbody fusion device in a disc space comprising a single cavity between adjacent vertebrae, comprising:
   creating a working channel to the disc space by placing a cannula through the skin and tissue of a patient using a transforaminal approach to the disc space;
   preparing the disc space through the working channel for bi-lateral placement of the at least one interbody fusion device, wherein
   preparing the disc space includes inserting a chisel through the cannula and into the disc space, the chisel including upper and lower cutting edges to remove a portion of the vertebral endplates and a curved shaft defining a curvilinear cutting path, wherein preparing the disc space includes inserting the curved shaft of the chisel into the cannula and moving the upper and lower cutting edges along vertebral endplates to prepare a cavity extending bilaterally across the adjacent vertebrae to receive the at least one interbody fusion device; and
   inserting the at least one interbody fusion device into the disc space through the working channel so that the adjacent vertebrae are bi-laterally supported by the at least one interbody fusion device.

2. The method according to claim 1, further comprising inserting a viewing element through the working channel; and preparing the disc space includes preparing the disc space with the viewing element in the working channel.

3. The method according to claim 2, wherein inserting the viewing element includes inserting the viewing element into the working channel to directly visualize the disc space.

4. The method according to claim 1, wherein creating a working channel includes:
   inserting a first dilator through the skin and tissue of the patient;
   sequentially inserting at least one more dilator over the first dilator;
   inserting the cannula over the last inserted dilator; and
   removing the dilators so that the cannula defines the working channel.

5. The method according to claim 4, further comprising connecting the cannula to a table based arm.

6. The method according to claim 1, wherein
   inserting at least one interbody fusion device comprises inserting a first fusion device through the cannula at a first bi-lateral location in the disc space opposite the cannula and inserting a second interbody fusion device through the cannula at a second bi-lateral location in the disc space adjacent the cannula.

7. The method according to claim 1, wherein preparing the disc space includes inserting a chisel in the disc space, the chisel having upper and lower cutting edges to remove a portion of the vertebral endplates.

8. The method according to claim 7, wherein the chisel has a curved shaft defining a curvilinear cutting path.

9. The method according to claim 1, wherein preparing the disc space includes inserting a shim through the working channel to maintain distraction of the disc space.

10. A method for inserting at least one interbody fusion device in a disc space comprising a single cavity between adjacent vertebrae, comprising:
    creating a working channel to the disc space by placing a cannula through the skin and tissue of a patient using a unitary transforaminal approach to the disc space;
    preparing the disc space through the working channel for bi-lateral placement of the at least one interbody fusion device, wherein preparing the disc space includes inserting a chisel through the cannula and into the disc space, the chisel including upper and lower cutting edges to remove a portion of the vertebral endplates and a curved shaft defining a curvilinear cutting path, wherein preparing the disc space includes inserting the curved shaft of the chisel into the cannula and moving the upper and lower cutting edges along vertebral end plates to prepare a cavity extending bilaterally across the adjacent vertebrae to receive the at least one interbody fusion device; and inserting at least one interbody fusion device into the disc space through the working channel along the unitary transforaminal approach so that the at least one interbody fusion device is positioned bi-laterally in the disc space to support the adjacent vertebrae.

11. The method according to claim 10, further comprising inserting a viewing element through the working channel; and preparing the disc space includes preparing the disc space with the viewing element in the working channel.

12. The method according to claim 11, wherein inserting the viewing element includes inserting the viewing element into the working channel to directly visualize the disc space.

13. The method according to claim 11, wherein creating a working channel includes:
inserting a first dilator through the skin and tissue of the patient;
sequentially inserting at least one more dilator over the first dilator; inserting the cannula over the last inserted dilator; and
removing the dilators so that the cannula defines the working channel.

14. The method according to claim 13, further comprising connecting the cannula to a table based arm.

15. The method according to claim 10, wherein inserting at least one interbody fusion device comprises inserting a first interbody fusion device through the cannula at a first bi-lateral location in the disc space opposite the cannula and inserting a second interbody fusion device through the cannula at a second bi-lateral location in the disc space adjacent the cannula.

16. The method according to claim 10, wherein preparing the disc space includes inserting a chisel in the disc space, the chisel having upper and lower cutting edges to remove a portion of the vertebral endplates.

17. The method according to claim 16, wherein the chisel has a curved shaft defining a curvilinear cutting path.

18. The method according to claim 10, wherein preparing the disc space includes inserting a shim through the working channel to maintain distraction of the disc space.

* * * * *